(12) United States Patent
Ouyang et al.

(10) Patent No.: US 12,420,478 B2
(45) Date of Patent: Sep. 23, 2025

(54) IMAGING PRINCIPLE-BASED INTEGRATED COLOR LIGHT 3D BIOPRINTING SYSTEM

(71) Applicant: ZHEJIANG UNIVERSITY, Hangzhou (CN)

(72) Inventors: Hongwei Ouyang, Hangzhou (CN); Renjie Liang, Hangzhou (CN); Yi Hong, Hangzhou (CN); Shufang Zhang, Hangzhou (CN); Oikai Li, Hangzhou (CN); Yiwei Zou, Hangzhou (CN); Feifei Zhou, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 380 days.

(21) Appl. No.: 17/616,041

(22) PCT Filed: Jul. 24, 2019

(86) PCT No.: PCT/CN2019/097471
§ 371 (c)(1),
(2) Date: Dec. 2, 2021

(87) PCT Pub. No.: WO2020/244037
PCT Pub. Date: Dec. 10, 2020

(65) Prior Publication Data
US 2022/0324163 A1    Oct. 13, 2022

(30) Foreign Application Priority Data

Jun. 4, 2019 (CN) .......................... 201910482826.9
Jun. 4, 2019 (CN) .......................... 201910483433.X
Jun. 4, 2019 (CN) .......................... 201910483826.0

(51) Int. Cl.
*B29C 64/135*    (2017.01)
*B29C 64/188*    (2017.01)
(Continued)

(52) U.S. Cl.
CPC .......... *B29C 64/135* (2017.08); *B29C 64/188* (2017.08); *B29C 64/255* (2017.08);
(Continued)

(58) Field of Classification Search
CPC ............ B29C 64/124–135; B29C 64/264–291
See application file for complete search history.

(56) References Cited

U.S. PATENT DOCUMENTS

2016/0107380 A1    4/2016 Smoot et al.
2018/0257297 A1*   9/2018 Matheu ............... A61L 27/3625
(Continued)

FOREIGN PATENT DOCUMENTS

CN    104589651 A    5/2015
CN    104669621 A    6/2015
(Continued)

OTHER PUBLICATIONS

Kelly, Brett E., et al. "Computed axial lithography for rapid volumetric 3D additive manufacturing." (2017). (Year: 2017).*

*Primary Examiner* — Susan D Leong
*Assistant Examiner* — Vipul Malik
(74) *Attorney, Agent, or Firm* — NZ Carr Law Office

(57) ABSTRACT

An integrally-formed three-dimensional (3D) bio-printing system capable of alternate feeding of multiple materials, comprising: an optical imaging unit and a light path conversion unit, wherein the optical imaging unit comprises an image processing unit and a projection unit, the image processing unit segmenting a 3D modeling graphic of a printed subject to form image information, the projection unit converting the image information into one or more optical images, and the light path conversion unit projects the imaged light paths into bio-ink that can be cured by light, so that the projected image can cure the bio-ink by means of the focus of light.

11 Claims, 14 Drawing Sheets

(51) Int. Cl.
  *B29C 64/255*  (2017.01)
  *B29C 64/286*  (2017.01)
  *B29C 64/336*  (2017.01)
  *B29C 64/393*  (2017.01)
  *B29K 105/24*  (2006.01)
  *B33Y 10/00*  (2015.01)
  *B33Y 30/00*  (2015.01)
  *B33Y 40/10*  (2020.01)
  *B33Y 50/02*  (2015.01)

(52) U.S. Cl.
  CPC .......... *B29C 64/286* (2017.08); *B29C 64/336* (2017.08); *B29C 64/393* (2017.08); *B33Y 10/00* (2014.12); *B33Y 30/00* (2014.12); *B33Y 40/10* (2020.01); *B33Y 50/02* (2014.12); *B29K 2105/24* (2013.01); *B29K 2995/0056* (2013.01)

(56) References Cited

U.S. PATENT DOCUMENTS

2018/0326666 A1* 11/2018 Kelly .................... B29C 64/264
2020/0376754 A1* 12/2020 Lambrecht ............. B29C 64/30

FOREIGN PATENT DOCUMENTS

| CN | 107050518 A | | 8/2017 | | |
|---|---|---|---|---|---|
| CN | 107148302 A | | 9/2017 | | |
| CN | 108567993 A | | 9/2018 | | |
| JP | H08201915 A | * | 8/1996 | | |
| WO | WO-2017048710 A1 | * | 3/2017 | ............. | B29C 35/08 |
| WO | WO-2018/018033 A1 | | 1/2018 | | |
| WO | WO-2019095600 A1 | * | 5/2019 | ........... | A61K 31/722 |

* cited by examiner

IMAGING PRINCIPLE-BASED INTEGRATED COLOR LIGHT 3D BIOPRINTING SYSTEM

CROSS REFERENCE TO THE RELATED APPLICATIONS

This application is the national stage entry of International Application No. PCT/CN2019/097471, filed on Jul. 24, 2019, and this application claims priority to Application No. 201910483433.X filed in China on Jun. 4, 2019, Application No. 201910482826.9 filed in China on Jun. 4, 2019, and Application No. 201910483826.0 filed in China on Jun. 4, 2019, the entire contents of all of which are hereby incorporated by reference.

TECHNICAL FIELD

The invention relates to a light-based 3D bio-printing system and also to biomaterials for printing uses.

BACKGROUND

In clinical practice, there are a large number of patients who cannot live a normal life because of necrosis of tissues and organs. At present, the main treatment methods still rely on antilogous tissue transplantation or allergenic organ donation. However, the donation of allogeneic tissues and organs is far from meeting the actual clinical needs. Besides, the transplantation of allogeneic tissues or organs also has the risk of rejection, which leads to the failure of transplantation. Therefore, there are still a large number of patients who cannot be treated or cannot receive effective treatment.

In recent years, with the development of tissue engineering and regenerative medicine, the construction of biologically active tissues and organs in vitro has become a research hotspot. However, traditional tissue engineering methods can only build tissue engineering tissues with simple structures, and there is no way to imitate tissues and organs in vivo from outside. 3D printing technology is widely used in tissue engineering and regenerative medicine as a more convenient and effective means of constructing three-dimensional structures. At present, the mainstream optical 3D printing methods include stereolithography (STL) printing and optical 3D method based on digital light processing (DLP).

DLP light curing printing and extrusion printing. The DLP photocuring printing equipment contains a liquid tank that can hold the resin, which is used to hold the resin that can be cured after being irradiated with ultraviolet light of a specific wavelength. The DLP imaging system is placed under the liquid tank, and the imaging surface is located at the bottom of the liquid tank. Through energy and graphic control, a thin layer of resin with a certain thickness and shape can be cured each time (the layer of resin is exactly the same as the cross-sectional shape obtained by the previous division). A lifting mechanism for lifting the tray is provided above the liquid tank, and the tray is stepped to form a layered forming surface between the tray (or formed layer) and the liquid tank, and a certain height is lifted up after each cross-section exposure is completed (The height is consistent with the layer thickness), so that the currently solidified solid resin is separated from the bottom surface of the liquid tank and bonded to the lifting plate or the resin layer formed last time. In this way, three-dimensional solids are generated by layer-by-layer exposure and lifting. The optical system of the DLP 3D printer is fixed, and the optical system can only print one layer thick at a time. Generally, the method of first raising and then lowering is adopted, that is, if printing with a layer thickness of 0.1 mm, it is first raised by 5 mm and then lowered by 4.9 mm. Each time the molding surface is on the liquid surface, the model is immersed in the material liquid after molding. However, this method will also have problems. The surface tension of the feed liquid will affect the thickness of the molding layer and the molding effect. Moreover, each molding surface is on the liquid surface, so every time the printing needs to fill the liquid tank, even if the actual material consumption of the entity to be molded is much smaller than the volume of the liquid tank, the liquid tank must be filled to ensure every time the molding surface is on the liquid surface, and the remaining material liquid cannot be used again after molding. In addition, the DLP photo-curing printing lifting mechanism is also immersed in the material liquid, and in order to make the molding surface on the liquid surface every time, it is necessary to balance the volume difference caused by the sinking of the lifting mechanism. Therefore, a balance weight must be set in the liquid tank. The lift mechanism, balance weight and tray are all located in the liquid tank, and the lifting mechanism and balance weight occupy the cross-sectional area of the liquid tank, resulting in an effective forming area (tray area) smaller than the cross-sectional area of the liquid tank and a small effective forming area.

The existing artificial soft tissue preparation method of extruded and light-cured composite molding includes the following steps: 1. Model the artificial soft tissue to obtain the artificial soft tissue model; 2. Process the contour of each layer in the artificial soft tissue model: use 3D Print the layering software to calculate the contour information of each layer in the artificial soft tissue model, and generate the contour information to run the extrusion nozzle; 3. Prepare the light-curing composite solution: first make the living cells, growth factors and collagen solution Mix to obtain a mixed solution, then inject a photocurable hydrogel into the mixed solution, and then add a visible light photo initiator to obtain a hydrogel composite that can maintain a certain shape; 4. The photocurable composite solution prepared in step 3 is Raw material, artificial soft tissue preparation using 3D printer: 4-1, control the hydraulic extrusion head to extrude the hydrogel compound on the working platform according to the running path to form a semi-solidified colloid layer; 4-2, carry out on the colloid layer Light curing to obtain a cured layer. The hydraulic extrusion head is fixedly connected with the light curing head. When the hydraulic extrusion head is in the working state, the light curing head is closed; when the hydraulic extrusion head is reset according to the movement trajectory during work, the hydraulic extrusion head is closed, and the light curing head is in Working status.

The disadvantages of this method of forming biological tissues are as follows. 1. No matter whether it is DLP or extruded, multiple materials cannot be used to collaborate to complete the forming task of a biological tissue, so mixed processing of multiple materials cannot be achieved. The living organism is a non-uniform mixing system containing multiple structures and multiple material components. The above method cannot complete the forming of the non-uniform mixing system. 2. The feeding and forming speed of DLP is fast, but there is a lot of wasted liquid and the one-time usage rate of the liquid is low. This also requires improved design of existing traditional printing, hoping to print bioactive materials with more complex structures.

However, human tissues and organs have complex assembly structures and a variety of components. The unevenness of tissues or cells is an inherent property of living tissues.

This requires an improved method for existing 3D printed bio-living materials or scaffolds, so that it is closer to the nature of natural living tissue, so that it has more medical application value.

SUMMARY

Thus, to construct biomimetic tissues/organs with physiological activity in vitro, it is necessary to imitate the structure and composition of natural healthy tissues and organs during 3D printing. Therefore, valuable living materials could be provided.

Based on the principle of volume imaging, the team of the present invention could be used for integrated printing of complex structures, and by installing channels for entering and exiting bio-inks at the upper and lower ends of the resin tank, bio-inks can be replaced during printing to imitate different components of tissue. Therefore, it is completely feasible to develop a set of integrated colorful light-based 3D bioprinting system to construct in vitro bionic tissues and organs with physiological activity.

One of the aspects of the present invention is to provide a 3D bioprinting system that can realize integrated molding and alternately feed multiple materials.

Therefore, in a first aspect of the present invention, a printing system is provided, including an optical imaging unit, by which the printed subject is converted into one or more optical images. In some embodiments, it also includes an optical path conversion unit; this unit allows the imaged optical path to be projected into a bio-ink that can be cured by the light, so that the focused light allows the formed image to photo-cur the bio-ink.

In some embodiments, the supply unit for supplying bio-ink and the discharge unit for discharging bio-ink are directly or indirectly connected to the unit containing bio-ink for replacement of different bio-inks. The bio-ink that is generally photo-cured is contained in the curing unit. In some embodiments, the curing unit may have a bio-ink from the feed unit.

In some embodiments, the image presented by the optical imaging unit comes from the image processing unit.

In some embodiments, the image processing unit includes a computer tomography module to process the three-dimensional image. Here, after the image processing, different image digital signals are formed, which are projected by the projection device, thereby showing that some parts of the main body or one layer of the multilayer structure need to be printed.

In some embodiments, the image processed by the image processing unit is a slice image of the three-dimensional modeled model rotated at a fixed angle with the central axis. The model composed of the slice images here is a 3D printed structure, which is bionic or has a structure capable of carrying biologically active cells.

In some preferred embodiments, the curing unit may be, for example, a quartz resin tank; the upper, lower, and outer sides of the curing unit are connected to the feeding unit and the discharging unit, respectively.

In other embodiments, the photo-crosslinkable bio-ink of the curing unit can be directly cross-linked by the focused image, and the resin tank is independent of the optical system.

The so-called independence, the position where the bio-ink is cured and the position where the optical imaging unit is are independent to each other; the movement of the two will not interfere with each other. Generally, the position where the bio-ink is cured (curing unit) remains stationary, and the optical imaging system is in a changing state. This changing state can be a change in position, or a change in optical imaging or light wave. In some modes, an optical path conversion unit may also be included, which changes the position of the unit relative to the curing unit. At this time, the projection device and the curing unit do not move, but rely on the light converter to transfer the projected image and convert it to the curing unit. When it is required to print a complex structure, an object is always a three-dimensional structure, always a three-dimensional structure, which makes it easy to adjust the angle and position of the optical path conversion unit, so as to carry out the overall curing of different materials. The details will be described in detail below in conjunction with specific implementation examples.

In this way, the curing position of the bio-ink remains stationary, and a more sophisticated and complex structure can be realized. This is because when bio-inks with different compositions are printed continuously (or cured) at the same time, the bio-ink is a fluid property, such as liquid property or semi-solid (non-solid). Light curing needs to be completed within a certain time; if the curing unit is in the process of moving, different bio-inks in the process of curing may be mixed, causing cross contamination. When in a fixed position, we let the light source change, so that the curing position or volume can be accurately controlled to achieve more precise printing, especially the generation of complex multi-dimensional structures, which has more practical application significance.

The change or conversion of light can be reflected as the change of the light focus position and the change of intensity, so as to realize the printing or processing of different structures in different parts, or more complex structures. Printing and processing here are interchangeable, meaning the same.

The curing unit may be a resin tank or a quartz tank. The purpose is to enable the real image projected by the optical system to be in the central area of the quartz resin tank and to realize the photo-curing of the bio-ink. The feeding unit is outside the optical system, and the bio-ink in the feeding unit is outside the photo-curing area of the optical system. During printing, the bio-ink can be photo-cured without moving the quartz resin tank. The spatial position of the optical system is independent of the quartz resin tank, which means that the movement of the optical system will not cause the movement of the quartz resin tank. In one mode, the curing unit includes an internal container for receiving bio-ink, wherein the internal container is fixed.

In some embodiments, the outer container includes a movable outer container, and the outer container can rotate around the inner container. In some modes, the rotation is circumferential rotation. It can be considered that the outer container rotates around the inner container. In this way, in the process of rotation, the light is fixed to cure the bio-ink, so that accurate printing can be achieved.

According to a second aspect of the present invention, provided is a printing system including an optical imaging unit, which allows a printed subject to form one or more optical images, and the image is projected into a printing and curing unit for photocuring.

In a preferred embodiment, the optical imaging unit includes an image processing unit and a projection unit.

In a preferred embodiment, the image processing unit includes a module that performs segmentation processing on the image of the printed subject.

In a preferred embodiment, the curing unit is connected to multiple discharge ports, and each discharge port of the multiple discharge ports corresponds to a different bio-ink, thereby excluding the bio-ink in the curing unit.

In a preferred embodiment, the curing unit includes a lifting platform, which can move upward.

In a preferred embodiment, the image is projected into the curing unit through the curing unit from bottom to top.

In a preferred embodiment, the curing unit is located between the lifting platform and the projection device.

In a preferred embodiment, the segmentation is a partial structure segmentation of the printed subject, and the segmented image is projected into the curing unit.

In a preferred embodiment, the system further includes a feed port connected to the curing unit. The feed port includes a detachable bio-ink device that can carry multiple different bio-inks.

According to a third aspect of the present invention, the present invention provides a printing device. The device includes an optical path conversion unit, and the unit can project one or more images generated from the projection device into a curing unit for curing.

Preferably, the curing unit includes a bio-ink container for containing bio-ink, and the image is projected into the bio-ink container.

Preferably, the positions of the optical path conversion unit and the curing unit are relatively rotated.

Preferably, the curing unit is fixed, and the optical path conversion unit is arranged in a circular motion around the curing unit.

Preferably, the optical path conversion unit projects the image into the curing unit through the reflection of light.

Preferably, the reflected light is perpendicular to the curing unit.

Preferably, the longitudinal axis of the curing unit is perpendicular to the image axis of the projection device.

Preferably, the device further includes a cartridge body containing a bio-ink container; the cartridge body surrounds the bio-ink container, and a liquid with a refractive index similar to the refractive index of the bio-ink is filled between the ink container and the cartridge body.

Preferably, the optical path conversion unit includes a lens and/or mirror.

Preferably, the lens converts the light from the projection device into parallel light, and the reflecting mirror is used to project the parallel light vertically into the curing container.

Preferably, the optical path conversion unit is rotatably disposed relative to the curing unit.

Preferably, the optical path conversion unit includes a mirror.

Preferably, the device further includes a rotation angle measuring device to measure the angle of rotation of the optical path conversion unit around the curing unit.

Preferably, it further includes a computer system that allows the angle measured by the angle measuring device to adjust the angle of the projected image.

According to a fourth aspect of the present invention, the present invention provides an integrated colorful light-based 3D bioprinting method based on the imaging principle. The method includes:

providing three-dimensional modeling graphics of the printed subject;

making the image processing unit segment the three-dimensional graphics to form image information;

making the projection device convert the image information into one or more images; and making the optical conversion unit transfer the image to the curing unit to photocure the bio-ink.

Preferably, the image processing unit includes the model file which can be read by the software Matlab.

Preferably, the Image Processing Toolbox in the software Matlab is used to segment the 3D model.

Preferably, the images are fused using the Image Blending Package in the software Matlab.

Preferably, find the central axis of symmetry of the model, make a plane containing the axis of symmetry, and output the mapping data of the 3D model on the plane; rotate the plane clockwise, cut once at a certain angle, and complete after the cutting process. The result file data after the processing is completed is obtained.

Preferably, the result file data is converted by a projection device to obtain one or more images.

Preferably, the optical conversion unit is moved in a circular motion around the curing unit.

Preferably, the optical conversion unit allows the vertical light to be converted into parallel light and is vertically incident into the curing container.

Instructions in Detail

Image Processing System In some system, the image processing system is based on the basic principle of computed tomography (CT). First, the two-dimensional slice digital image is obtained from the three-dimensional model of the object to be printed. Then, each slice image is projected along a 360° direction at a certain angular interval to obtain a one-dimensional line integral along each projection direction. The angle here can be any angle, for example, different angles such as 1°, 2°, and 5°. In a certain projection direction, the line integrals of all slice images are superimposed along the slice cutting direction to obtain a two-dimensional projection image in the projection direction.

The smaller the angular interval of the projected image, the higher the resolution of the printed object. In theory, a higher resolution can be achieved when the projection interval is 1°. In some methods, the projected image needs to be filtered to avoid the phenomenon of "star-shaped artifacts" in the reconstructed object. Since the filtered projection will inevitably introduce negative pixel values, in order to achieve normal projection and obtain the highest possible print resolution, this system designs and applies an iterative optimization algorithm in order to obtain the highest print quality.

Image processing is the pre-processing of the three-dimensional modeling of printing. It is hoped that the main body of the modeling will be divided into different pieces, so that different complex structures can be accurately processed. As we all know, organisms are not in the state of continuous mean, but in the state of discontinuous non-mean. In these complex structures, only the main bodies of these processes are divided infinitely or precisely to form different division units. The texture and structure between these divided units are not exactly the same, so that they can be processed with different bio-inks and processed according to the divided units, and finally the processing of complex structures can be completed. The image segmentation can be vertical or horizontal, and then the three-dimensional image of the printed subject is divided into multiple image units. Each image represents a layer structure that needs to be cured by light. The final body is composed of countless images and a complete structure composed of countless cured layers during light curing.

When performing segmentation, it is actually analyzing or decomposing the complex structure to form different image units, and layering and curing the image units. These image units are mainly based on optical images, and generally these images are implemented by a projection device. Allow the image unit to be projected into the bio-ink to cure the image unit. After curing is complete, if the structure indicated by the next image unit is different from the structure indicated by the previous image, such as texture, density, whether or not if it contains voids, etc., you need to replace different inks for curing. At this time, let the ink of the previous image be excluded, add another corresponding different ink to cure the next image, and so on, you can achieve the so-called "color printing". If the higher the resolution of the image processing and the smaller the image unit, the tighter and finer the printing effect.

When performing image projection, the image is not directly projected into the curing unit, but is converted into the optical path, so that the light of the image is converted through the optical path, so that the light is perpendicular to the curing unit, thereby curing the light. Generally, the intensity of the light of an image is the same (when the printed area corresponding to the image is of the same material), curing is performed where there is light, and curing is not performed where there is no light (for example, the corresponding printing material is the same, but it has Structures such as holes and holes). The light used for curing is the light converted from the optical path. It can be understood that image processing is to continuously divide the three-dimensional model to form multiple different image units. Each image unit represents a surface of the main body to be printed. The length or thickness of the surface can be freely set, and the surface can be any shape, such as rectangular, round. The thickness can also be a few microns, a few millimeters. If the composition of the printed main image is composed of multiple different structures, the image processing is divided according to different structures, thereby obtaining different divided image data.

The specific image processing method is described by using FIGS. 8, 9 10, 11 examples.

1. Use C4D software to model and create the target printing structure, for example, it can be a columnar structure with two layers on top and bottom, as shown in FIG. 8 on both sides of the structure, or three-dimensional construction of different structures, any of the different internal structure can be achieved.

2. Separate the upper and lower layers of the model, and export them to the upper structure (upper.stl) and lower structure (bottom.stl) format files, as shown in FIG. 9 and FIG. 10.

3. Use Matlab software to read the upper and bottom files (.stl).

4. Use the Image Processing Toolbox of Matlab to segment the images of the upper and bottom 3D models (the degree of segmentation is 0.9°).

5. Use the Image Blending Package of Matlab to fuse the two models of upper and bottom, and make the holes correspond.

6. Find the central symmetry axis of the upper and bottom models, make a plane containing the symmetry axis, and output the mapping of the 3D model on the plane with digital embodiments.

7. Rotate the plane in a clockwise direction and cut every certain angle. As shown in FIG. 11, after the cutting process is cycled, the result file after the processing is completed, and the output is digital embodiments.

The Projecting Device and the Optical System

In some ways, the core part of the optical system is the DLP projector 1005/ the stepper motor 1004. The DLP projector is a fixed device, which is responsible for converting the image-processed information into an optical image (one or more images). The image data here comes from the image of the three-dimensional model processed by the image processing system.

The outgoing light of the projector 1005 is projected into the container containing the bio-ink through the optical path conversion system or the conversion unit 1002, so that the image to be cured is presented in the container. The image here is the same as the generated optical image or the processed image. These images are characterized by light. These lights are converted by the optical path into the curing container, so that the light is focused and used to cure the bio-ink. The cured structure can correspond to the image one by one.

In some embodiments, the light emitted from the projector is converted into parallel light by the lens 1003 and irradiated to the reflecting mirrors 10129, 10128, and 10127, and then reflected and irradiated into the container 1102 containing bio-ink. Here, the optical path conversion unit may include a lens/mirror.

In some ways, the light is projected into the curing container. In this process, the light may be disturbed. Ideally, the light from the reflection hopes to be 100% projected into the curing container, and the direction does not change, so that the size and quality of the projected image in the curing container are consistent with the processed image; and it is also hoped that the projected image is consistent with the actual segmented image. The so-called consistency refers to the size, position and pixels, etc. However, this is not easy. This actually involves light interference and image deformation.

In one way, when the optical path conversion unit moves around the curing unit or the periphery of the curing container, the curing container is generally curved, such as a round wall, so that the image can be projected into the bio-ink of the container within a range of 360 degrees. However, the container has a container wall with a certain thickness. When the parallel light from the mirror 1002 is projected on the wall of the solidified container of the cylinder, it is also desired that the direction of the parallel light enters the bio-ink without changing the direction. However, since the wall of the cylinder is not a mirror surface, light refraction or reflection (a surface that is not perpendicular to the parallel light) will occur on the walls of other curved surfaces, resulting in image distortion and a reduction in light intensity. Therefore, in order to reduce refraction, a polarizing unit is provided on the periphery of the curved wall. This unit can correct the direction of light entering the container, and try to make each light perpendicular to the curved wall as much as possible, thereby reducing the deviation of light. In one embodiment, the polarizing unit can be the original of a square box, and the liquid between the square box and the curved wall is filled with liquid with similar refractive index to the bio-ink, so that the light entering the curing container is always vertical, and the image's shape won't change. In some preferred ways, in order to reduce the refraction of the projection light from the air into the resin tank (or curing container 1102), the resin tank is placed in a square box 1101, which contains a liquid with a refractive index similar to that of the bio-ink 1104, and the main light of the projector is always incident perpendicular to the surface of the square box, so that the light entering the curing container can always be kept vertical. Here, the square box is located outside the curing unit and surrounds the curing unit. Of course, it may not be a square box, but may be a container of any shape matching the curing container. The container is provided with a curing container. The curing container is used to carry bio-ink. The bio-ink is generally liquid. When it is irradiated by light, it can be cured by light to become a solid state. The square box-like structure here can also be integrated with the optical path conversion system. When the optical path conversion unit moves, the square box also moves around the curing unit. This keeps the reflected light incident vertically into the curing container. It can be understood that the square box and the curing unit can also be in a unitary structure to maintain a fixed state, allowing the optical path conversion unit to rotate relatively to project light into the curing container. The curing container here can also be of any shape, such as a rectangular parallelepiped, a cylinder, etc.

In other embodiments, the polarizing unit may be a glass prism and/or a cylindrical lens. In some methods, a glass prism and a cylindrical lens are provided on the periphery of the curing container, wherein one side of the glass prism is curved and fits the curved surface of the ink container, and the rest is flat. Fill the space between the bio-ink container and the polarizing unit with prism oil with the same refractive index to the glass prism, used for light penetration and lubrication when rotating. Cylindrical lens is used to compensate the deviation of the focal plane of the image caused by the refractive index deviation between the glass prism and the ink. So that the light enters the curing container, and the image keeps the same size as the projected image. For example, as shown in FIGS. 19 and 20, the positional relationship between the curved container wall 6001, the glass prism 6002, and the cylindrical lens 6003 has lubricant at the junction of the container wall 6001 and the glass prism 6002, on the one hand, reducing friction when the glass prism rotates around the container; on the other hand, the refractive index of the oil is the same as the prism, so that the direction of the light entering the container is kept as parallel as possible. When the parallel light passes through the cylindrical lens and enters the glass prism, passes through the oil, and then passes through the wall of the container; the parallel light is still in the container, so that the shape and position of the image formed in the container and other cured images maintain an accurate position. Thus the structure cured in the container is consistent with the actual design of the modeled structure, otherwise the accuracy of printing will not be enough, especially for complex and small structures, and more accurate printing is needed. This is actually to make the parallel light from the mirror project as much as possible into the ink of the curing container, so that the direction of the light does not change; it is all parallel light. For example, as shown in FIG. 11, the image processing system performs longitudinal cutting according to the central axis, and cuts into different rectangular parallelepipeds. The rectangular parallelepiped is actually a longitudinal section of the cylinder (for example, a rectangular parallelepiped). These images pass through the image processing system, and then enter the projection equipment, and then project a rectangular parallelepiped surface through the projection instrument. This surface forms a rectangular surface in the container containing the ink through the projection and reflection of light. At the same time, where the light is irradiated, the light passes through the ink. The ink is focused and cured on the surface of the formed rectangular parallelepiped to form a cured rectangular parallelepiped surface. When the next side needs to be printed, continue to let the projector project the next image, and then pass through the optical path turning system to generate another figure in the container with ink; and the focus position changes, so the optical path needs to be made turn to focus the light on another plane to allow the bio-ink to solidify.

When there is a hole (for example, the cutting plane 106 in FIG. 9), what is actually projected is not a complete plane, but a plane with a local gap. The projection is a projected image with a gap. The light is not focused at the gap so that curing does not occur. In this way, through continuous circulation, a complete three-dimensional structure is printed in the bio-ink.

During the printing process, the stepper motor 1004 drives the optical path conversion unit 1002 to make a circular movement around the curing unit. In some embodiments, the mirror and the square box rotate synchronously; the projector and the resin tank are fixed, or the lens is also fixed. The center of rotation of the mirror and the square box coincide with the geometric center of the curing unit, such as the resin tank. According to the preset angle interval of the image processing system, each time the stepper motor rotates through an angle, it drives the mirror and the square box to rotate by an angle in the same direction. At the same time, the projector quickly switches to the next projected image to complete a projection direction Exposure. After a 360° exposure, a specific exposure amount distribution will be formed in the resin tank, and the positions exceeding the bio-ink photo-curing exposure threshold will be cured and formed, and the remaining positions will still be liquid, thus achieving 3D printing of the model.

Therefore, how to transform or rotate light is determined according to different image segmentation methods. In some ways, it may be segmented in a circumferential tangent manner to form different image units. For example, the division method in FIGS. 8-11 is divided in the form of a circle. For example, the upper and lower cylinders have different textures; but the upper structure itself has the same texture except for the holes, so one kind of bio-ink is sufficient. However, if the superstructure itself has other different properties, such as different hole sizes, different positions, or different textures, image processing needs to continue to be decomposed, knowing to decompose into different image units to perform a single image Curing printing.

The two-layer structure shown in FIG. 8 is printed, and the optical system is described in conjunction with FIG. 13.

1. Import the file processed by the image processing system into the optical system.
2. Turn on the DLP projector to produce different projection optical images, usually one pair of images.
3. Inject the GelMA, in the feeding unit 1, into the inner container from the below layer; the height of the bio-ink is slightly larger than the that of the underlying structure.
4. Start the printing process, the projected image of the DLP projector passes through the optical path turning system and is projected into the container loaded with bio-ink. The inner container 1102 is loaded with bio-ink and is fixed, and the outer container (square box 1101) rotates together with the rotating platform. DLP projected images of different angles of the model can rely on the optical path turning system to perform corresponding angle transformation to achieve 3D printing of the model. The realization method is that the stepping motor drives the optical path turning system to rotate through the transmission device so that the projected image can be projected arbitrarily along the 360° direction. (The PC program controls the stepper motor rotation and the synchronous switching of the projector image)

5. After the optical path turning system rotates 360°, the bio-ink GelMA in all angle projection areas is solidified and formed, and the remaining positions are still liquid, and the printing of the underlying structure is completed.

6. The discharge unit draws all uncured bio-ink GelMA from the bottom of the inner container. Then, the feeding unit 2 equipped with SilMA injects the bio-ink SilMA into the resin tank from the below inner layer of the container. The height of the bio-ink is slightly larger than the top surface of the structure corresponding to the resin tank.

7. Repeat steps 4 and 5 to complete the printing of the entire model in FIG. 8.

FIG. 12 is a microstructure diagram of each layer, wherein the top views of different cavity sizes reveal that the side holes and the top holes are arranged in the same way. At the same time, the fluorescence structure of 400 um was observed under a fluorescence microscope. In this way, complex structures can be printed more finely.

In some methods, the optical path conversion unit can perform relative up and down movements in addition to circular movements around the curing unit; alternately circular movements and up and down movements can also be set freely. These setting methods are determined according to the main body of printing. If different positions inside the printed subject have different structures, such as the same printed subject, similar to FIG. 9; except for the voids, the structure near the lower 102 is loose, while the texture near the upper surface is tight; or the entire structure has gradually transitions from loose to tight from the lower and upper surfaces. When printing such a structure, for three-dimensional image processing, the image is first divided horizontally, the loose structure and the precise structure are divided very horizontally, and then the material of the same texture is divided vertically. If the texture structure is in a transitional state, but when performing image segmentation, the accuracy of the segmentation needs to be high, so that the texture in each image is basically the same; however multiple images may be different, when printing, you need to change the ink multiple times and adjust the angle of light projection multiple times. For example, when the first image represents the underlying loose-textured material, it is cured with the pattern of the loose material configured, but the second image represents the printing of the compact structure. At this time, you can replace the bio-ink representing the tight texture, and then move the light conversion system upward to cure the dense surface on the loose surface. There may be no peripheral movement at this time, but there is up and down movement. If it is continuous or loose from the lower layer to the upper layer, it can be divided horizontally and vertically. Each image unit that is finally divided represents a printing and curing unit. This unit can be very large or small. Even if the area is a few microns, a few millimeters or centimeters, etc., then the so-called image unit only needs a beam of light when curing.

In short, the size analysis and segmentation of the image are done by the image processing unit, and the projection device reflects the image of the image segmentation, and then the optical path conversion can print the cured layer that is the same size as the image or is scaled up or down.

Rotation Angle Detection Device

In other solutions, the system equipment includes a rotation angle detection device, which is connected to the computer system. Rotation angle detection device has two functions. one is monitoring and controlling the rotation angle, and the other is correcting the image. In the present invention, the relative positions of the reflecting mirrors are generally fixed and different. These reflecting mirrors move around the curing container in a circumferential direction, that is, they move in a circle around the curing container. After the image from the projection device passes through the lens, the direction of the light has changed, at least into vertical light, such as parallel light. The parallel light enters the curing container to form an image. However, when it is necessary to rotate to print the next image, no matter what angle the rotation is, the angle between the projection mirror and the reflecting mirror in the horizontal direction changes, so that the direction of light from the projection mirror illuminates the reflecting mirror 10129 will change (compared to the previous image). Although the light is reflected twice or multiple times, the image itself will change the angle in this case, and the shape of the image may not change, but the angle of the image will change, so that the angle of the image projected into the curing container will change, which will cause errors in the printed structure. At this time, the rotation angle detect instrument monitors the horizontal rotation angle of the reflecting mirror in real time, and enters the actual angle into the computer control system. The computer calculates and allows the projection angle to be compensated in advance to ensure that the light angle of the projected image does not change after passing the lens and reflection.

For example, in FIG. 18, when the first projected image is 0 degrees, through lens and the reflected, optical path are converted. It is still projected into the curing container at an angle of 0 degrees. But when the mirror is horizontally shifted by a certain angle (For example, 45 degrees), if the projection device still reveals the second image of 0 degrees, according to the above explanation, the second image projected onto the curing container is also at an angle of 45 degrees, so that there is an angle deviation from the first image of 0 degrees, which is not consistent with the actual image to be printed. In order to reduce such errors, the rotation angle is measured by a rotation angle detection device, and then input into a computer system. The system performs calculations so that the projected image is projected at an angle of 45 in advance, and then passes through the conversion of the optical path to allow the projected image to an angle of 0 degrees into the curing container so that the angles of the two images are the same. It can be understood here that when the angles of the two images to be printed are the same, it is necessary to change the angular position of the projected image. This change is an adjustment made because the angle between the projection and the reflecting mirror rotation changes. If a certain angle is required between the printed images, it is still necessary to monitor the rotation angle by the rotation angle detection device to adjust the angle of the projected image, so that it is consistent with the angle between the designed images.

According to a similar explanation, when rotated 90 degrees, the projected image also needs to be adjusted to 90 degrees by calculation in advance. As can be seen from FIG. 18, the 0-degree image is the same size as the 90-degree image, but in different direction. Different angles can ensure that the angle of the image projected on the curing container is 0 degrees.

The method of adjustment here is to filter the projected image. Negative gray pixels are inevitably introduced into the filtered projection image. The program uses an optimization algorithm by gray thresholds constraining to eliminate negative gray pixels to obtain an optimized projection image that the projector can display. The optimization algorithm is shown in FIG. 21. Determine the exposure distribution threshold of bio-ink gelation through experiments, determine the constrained gray according to the exposure threshold, and use this gray value to constrain the projection image to ensure the correct exposure distribution of the final bio-ink, that is, the exposure of the model where the It is solidified above the threshold, and the exposure at the remaining positions is still liquid below the threshold.

The device drives the rotating platform to rotate through a stepping motor, so that the projected image of the projector can be projected onto the bio-ink in any direction through the optical path turning device. The projection image of the projector is switched synchronously with the rotation of the stepping motor. Stepping motor and projector are controlled by PC program. The control program is based on Boost:: Asio library in C ++ language, and the serial communication protocol is RS-232 communication protocol. During the rotation of the platform, the optical path of the optical path turning device determines that the projected image projected on the bio-ink will rotate with the rotation of the platform, and the angle of platform rotation per unit time is equal to the angle of rotation of the output image. Therefore, during programming, the projected image in each direction is rotated into the memory by a corresponding angle in the reverse direction of rotation, and then sent to the projector to ensure that the image projected on the bio-ink will not rotate.

Of course, the advantage of this method is to ensure the accuracy of the image, that is, the accuracy of the angle of the printed image. This is because the rotation of original structure 1002 where the reflecting mirror is driven by the stepping motor rotates. This is a mechanical structure movement, and there must be mechanical errors between the various parts. When printing precision structures, there is a mechanical error for each angle of rotation. When the cutting angle is 0.01 degrees, a three-dimensional structure has 36,000 images longitudinally cut. Each sub-image needs to be projected once and exposed once, then 36,000 rotations are needed. larger mechanical error, more actual printing images and smaller angle, all lead to greater mechanical errors. The rotation angle detection device is used to monitor the change of angle, which can accurately measure the change of the rotation angle, and adjust the angle of the image according to the change, thereby also overcoming the mechanical error and caused by the change in the angle of the image.

Feeding Process

The feeding unit feeds the curing container, such as a quartz resin tank, and the amount of each feeding is substantially equal to the amount of bio-ink corresponding to the highest height of the target structure at the stage of molding. The substantially equal refers to the amount of feed material can meet the amount of bio-ink required for molding. In some embodiments, the number of feeding units is ≥2. Each feed unit has its own independent barrel and feed rod, which were connected with a quantitative drive mechanism. But there is a common outlet at the bottom of the quartz resin tank, the feed rod is connected to the quantitative drive mechanism. The feeding rod pushes the bio-ink in the barrel to flow out from the discharge port, and the bio-ink flows into the quartz tank to reach the target height. The discharge port at the bottom of the quartz resin tank can avoid the mechanical impact of the bio-ink on the formed structure when feeding. There are multiple feeding units, which are used to provide bio-inks with different properties to realize the generation of heterogeneous bio-materials.

The feeding process is controlled by the controller and the sensor, which control the feeding of the ground driving mechanism. Preferably, a certain feeding unit is designated for feeding, or a plurality of feeding units alternately realize the feeding-photocuring-discharging-re-feeding-photocuring process. For example, there are two units: the first feeding unit feeds and cures light, and then the discharging unit drains the uncured bio-ink from the first feeding unit. Then, the second feeding unit is used for feeding and light curing, so as to realize the cross feeding of different units. Or, multiple feeding units feed at the same time, and then photocuring after the feeding is completed. For example, there are two units: the first feeding unit and the second feeding unit feed at the same time. The sum of the feeding amounts of all the units meets the amount of liquid required for forming the current layer. And then photocuring after the feeding is completed. Or, one or several forming stages are fed by a specified feeding unit, one or several forming stages are fed by multiple units at the same time, and one or several forming stages are fed by multiple units alternately. Or, specify a certain feeding unit to feed, and other units to suspend work. In this way, a single material print is formed.

Quantitative Drive Machine

The quantitative driving machine is used to quantitatively push the feeding rod, and the quantitative driving machine control the feeding method. In some preferred solutions, the quantitative driving machine includes a feeding driving member, and the connection between and feeding rod. Preferably, the feed driving member includes a clamp, and the feed rod is clamped in the clamp to realize the connection between the feed driving member and the feed rod. When the clamp releases the feed rod, the feed rod disengages from the feed drive member. Feeding drive parts adopt motor and transmission machine (such as screw machine), electric push rod, air cylinder, etc.

Preferably, each cartridge has its own cartridge holder, and the cartridge is fixed to the cartridge holder. Preferably, the cartridge holder includes a fixing portion and a connecting portion with a robot arm. The fixing part fixes the material barrel to ensure the stability of the discharge, and the connection part of the robot arm realizes the replacement of the material barrel.

Discharge

In multi-material printing tasks, it is sometimes necessary to drain the first bio-ink before adding the second bio-ink. In some preferred solutions, the printing system has a discharge unit. Preferably, the discharge unit includes a discharge port located at the bottom edge of the quartz resin tank, a discharge pipe connected to the discharge port, and a negative pressure suction device. After the first bio-ink is printed, the discharge unit starts negative pressure suction to suck the remaining uncured bio-ink. After the current bio-ink is drained, the second feeding unit works and the second bio-ink is added to avoid the mutual influence and interference of the two bio-inks.

Material and Bio-Ink

In this invention, the material and bio-ink refer to a material or mixture used for processing by the printer. When processing with the 3D printer of this invention, some existing biomaterials can be used for printing. For example, many materials including natural polymers: collagen, silk fibers, gelatin, alginate, and synthetic polymers, polyethylene glycol (PEG), or any combination of them can be processed by the printer of this invention. These are used as bio 3D printed materials and are also called "bio-inks". Although the materials themselves are traditional materials, they can all be printed using the inventive printing method. The printed biological material has a three-dimensional space structure, or has a thinking space, and can be provided with any through holes.

In some systems, the cartridge is a container containing different materials, and different cartridges can be used to contain the same material. Optionally, different materials or bi-inks can be contained in the barrel. For example, barrel A contains one biomaterial, barrel B contains another biomaterial, the properties of the two materials are not the same. using the printing technology of this invention can realize the printing of complex biological tissues or organs. This is because a biological organism or organ is not uniform in structure, but has differences in structure or biological properties. For example, mammalian skin material has an epidermis, a dermis, and the dermis has blood vessels and tissues connected to muscles. The structure of these different parts is different, the thickness is different, and the transitional structure between each tissue is also different. This difference also including density, pore size, etc. In this way, if printing by traditional printing is required, all structures or tissues are the same, and by the printing technology of this invention, biological materials of different structures can be processed at once.

In some systems, the bio-ink described in this invention can be mixed with stem cells for processing or printing. In this system, the materials serve as a scaffold structure, and the cells can be differentiated as active costs, and ultimately, form active tissues. Of course, you can also print out the scaffold structure, and then let the stem cells fill the space of the skeleton, and eventually form a living tissue. In short, the newly designed printing feed of this invention can print any suitable material.

In some specific ways, this invention provides a new 3D printed bio-ink, also known as a new material. In some specific embodiments, this invention provides a light-controlled 3D printing bio-ink or material, the material includes a light-responsive cross-linking group modified macromolecule, ortho-nitrobenzyl phototrigger modified macromolecule, light Initiator. In some examples, it also includes water, such as deionized water.

In some preferred embodiments, the final mass concentration of the photoinitiator is 0.001%-1% based on the mass of deionized water.

In some preferred embodiments, the graft substitution ratio of the light-responsive crosslinking group in the macromolecule modified by the light-responsive crosslinking group is 10%-90%, and the light-responsive crosslinking group is methacrylamide, methyl alcohol acrylic anhydride, glycidyl methacrylate or acryloyl chloride.

In some preferred embodiments, the graft substitution rate of the ortho-nitrobenzyl phototrigger in the macromolecule is 1%-100%.

In some preferred embodiments, further, the ortho-nitrobenzyl phototrigger modified macromolecule is represented by formula (I), $R_1$ is —H or selected from —CO $(CH_2)_xCH_3$, —CO$(CH_2CH_2O)_xCH_3$, —CO$(CH_2)_x$ $(CH_2CH_2O)_yCH_3$ ester bond, or selected from —$(CH_2)_x$ $CH_3$, —$(CH_2CH_2O)_xCH_3$, —$(CH_2)_x(CH_2CH_2O)_yCH_3$, ether bond, or selected from —COO$(CH_2)_xCH_3$, —COO $(CH_2CH_2O)_xCH_3$, —COO$(CH_2)_x(CH_2CH_2O)_yCH_3$ carbonate bond, or selected from —CONH$(CH_2)_xCH_3$, —CONH $(CH_2CH_2O)_xCH_3$, —CONH$(CH_2)_x(CH_2CH_2O)_yCH_3$ isocyanate bond, where x and y≥0 and are integers. $R_2$ is —H or selected from —O$(CH_2)_xCH_3$, —O$(CH_2CH_2O)_x$ $CH_3$, —O$(CH_2)x(CH_2CH_2O)_yCH_3$ substituent, where x and y≥0 and are integers. $R_3$ is selected from the amino-based bond —O$(CH_2)_xCONH(CH_2)_yNH$—, halogenated-bond —O$(CH_2)_x$— and carboxyl type bond —O$(CH_2)_xCO$—, where x and y≥1 and are integers. $R_4$ is —H or —CONH $(CH_2)_xCH_3$, where x≥0 and is an integer. $P_1$ is a macromolecule.

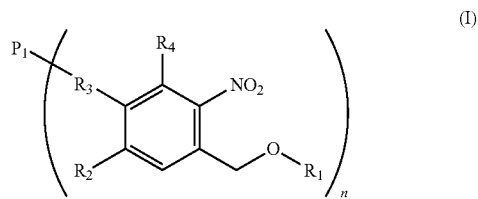

Further, it is preferred that the ortho-nitrobenzyl type optical trigger is o-nitrobenzyl.

In some preferred embodiments, the natural biological macromolecules in the macromolecules modified with photoresponsive crosslinking groups and the macromolecules modified with ortho-nitrobenzyl phototrigger are one of dextran, hyaluronic acid, gelatin, sodium alginate, chondroitin sulfate, silk fibroin, chitosan, carboxymethyl cellulose or collagen, polyethylene glycol or citric acid polymer (PEGMC).

In some preferred embodiments, the photoinitiator is 2-hydroxy-4'-(2-hydroxyethoxy)-2-methylphenylacetone (2-Hydroxy-4'-(2-hydroxyethoxy)-2-Methylpropiophenone (12959) or phenyl (2,4,6-trimethylbenzoyl) lithium phosphate (lithium phenyl-2,4,6-trimethylbenzoylphosphinate, LAP); the photoinitiator The mass ratio of macromolecules modified by grafting with photoresponsive crosslinking groups is 1-3:100.

In some preferred embodiments, the graft substitution rate of the macromolecule modified by the photoresponsive crosslinking group is 10%-30%; the graft substitution rate of the macromolecule modified by the ortho-nitrobenzyl phototrigger is 1%-20%.

In some preferred embodiments, the light-responsive crosslinking group modified macromolecule is methacrylic anhydride modified gelatin with a graft substitution rate of 10%, and methacrylamide modified with a graft substitution rate of 90%. Gelatin, methacrylic anhydride modified gelatin with a graft substitution rate of 40%, methacrylamide modified gelatin with a graft substitution rate of 20%, methacrylic anhydride modified collagen with a graft substitution rate of 30%, Chondroitin sulfate modified by methacrylic anhydride modified by 90% graft substitution or carboxymethylcellulose modified by methacrylamide modified by 10% graft substitution, acryloyl chloride modified by graft substitution rate of 10% polyethylene glycol, one of dextran modified by glycidyl methacrylate with a graft substitution rate of 20%.

In some preferred embodiments, the ortho-nitrobenzyl phototrigger modified macromolecule is one of the ortho-nitrobenzyl-modified hyaluronic acid with a graft substitution rate of 100%, ortho-nitrobenzyl-modified sodium alginate with a graft substitution rate of 50%, ortho-nitrobenzyl-modified chondroitin sulfate with graft substitution rate of 10%, ortho-nitrobenzyl-modified gelatin with graft substitution rate of 30%, ortho-nitrobenzyl-modified silk fibroin with a graft substitution rate of 90%, ortho-nitrobenzyl-modified collagen with a graft substitution rate of 100%, ortho-nitrobenzyl-modified chitosan with a graft substitution rate of 10%, or o-nitrobenzyl modified citric acid polymer (PEGMC) with a graft substitution rate of 10%.

In some preferred embodiments, the final concentration of the macromolecule modified by the light-responsive cross-linking group is 3%-10% by mass in deionized water, and the final concentration of the macromolecule modified by the optical trigger of ortho-nitrobenzyl group is 2%-4% by mass in deionized water, and the final mass concentration of the photoinitiator is 0.03%-0.2% by mass in deionized water.

The invention also provides an application of the light-controlled 3D printing ink in the repair of skin damage. The invention also provides an application of the light-controlled 3D printing ink in repairing articular cartilage defects. Further, the application is: printing the light-controlled 3D printing ink into a scaffold using a 3D printing technology based on digital light processing (DLP) and implanting it into the location of a skin defect to achieve skin tissue repair.

The invention utilizes the principle that the ortho-nitrobenzyl type optical trigger generates aldehyde groups after being excited by light, and the generated aldehyde groups and amino groups can react to form a strong chemical bond. At the same time, the light-responsive macromolecule modified by the cross-linking group is rapidly cured under light. Double cross-linked network enhances mechanical properties, 3D printed porous fine structure can achieve the purpose of rapid repair of defects, is an ideal light-controlled 3D printing ink for repair of skin defects or osteochondral defects. The material here can exist in any form, and can exist in solid form. When needed, it is configured to be printed in liquid form, or directly configured in liquid form. When printing is required, print processing is performed directly.

Here, materials and bio-inks are interchangeable. Generally, materials used for printing and processing can be called materials, and can also be called inks or bio-inks. The materials or inks here can include some active ingredients, such as stem cells, cells or other ingredients are included. Of course, only the material or ink itself is printed or processed, and then the active ingredient can be added.

The Printing Device

In some ways, the present invention provides a printing apparatus, such as the structure illustrated in FIGS. 13-17. In some embodiments, the printing device includes a photo-curing unit, and the curing unit has a container 1102 that can contain bio-ink; and a feeding system and a discharging system may be connected to the container. Generally light curing occurs in the bio-ink 1102 in the container. In some embodiments, the curing unit or the curing container is fixed. The printing device further includes an optical path conversion unit 1002 that can move relative to the curing unit. This unit converts the light of the image from the projection device into the curing unit to realize the curing printing of the light. In some ways, the optical path conversion unit includes a lens 1003 and/or a mirror 10129 to change the direction of light. In some ways, the projection device projects an image into the lens 1003. The lens realizes the conversion of the optical image from the projection device into parallel light. The parallel light reflects the light through the mirror and is projected into the light curing container 1102 to achieve the curing of the tube. In some ways, the reflection mirror may be one or more reflections at different angles to change the optical path. For example, FIG. 17 is a structural schematic diagram of optical path conversion in an embodiment of the present invention. The projection device 1005 projects an image 6000 into a lens 1003. The image here is an image-processed image unit, which represents the smallest unit that needs to be printed. The light incident on the lens 5001 is converted into light 5003 by the lens 1003 parallel to the mirror 10129 to realize the first change of the optical path; then the light is projected into the mirror 10128, and next the second change of the optical path. The last light 5004 is projected into the mirror of 10127. The change of the optical direction is realized to become parallel light, which is projected into the curing container 1001 to cure the light. The image of the general image unit 6000 is finally projected into the curing container through the change of the optical route, and has an image 5000. The projection of the light realizes the curing of the bio-ink, thereby completing the printing of a pair of images. In some ways, the unit including the mirror can make a circumferential movement around the curing container 1001, and the circumferential movement generally means a circular movement. The circular motion can be a 360-degree motion or a certain arc motion. In some ways, the mirror is arranged in an optical path channel, which realizes the change of light direction. The optical path 1002 realizes the overall rotation setting to surround the rotation setting of the curing container 1001. The optical path is fixed on the rotating structure 1002. The rotation of the rotating structure causes the optical path to change, thereby realizing the rotation of the optical path. The rotation 1002 of the rotation structure has a bracket structure 10124, and the direct structure is connected with a rotation shaft 10143, which is connected to the stepping motor 1004 to realize the rotation of the entire structure. The rotating radian or angle is the angle after digital processing when the image processing is divided. Of course, when the optical path needs to be moved up and down relative to the curing unit, a motor that drives the optical path to move up and down is required. The motion of these motors or stepper motors can be automatically controlled by computer software, and the control parameters can be some parameters in the image processing data to know the trajectory and parameters of the motion. Of course, in order to prevent outside light from entering the optical path channel or interfering with the light projected by the projection device, a fully enclosed channel can be implemented between the projection device and the lens or optical path channel, thus avoiding the entry of outside light. When reflected light is projected into the light curing unit, a close cooperation is also achieved to prevent the entry of external stray light and interfering with the light curing.

In some ways, it also includes a rotation angle monitoring device, which monitors the angle change, so as to input the degree of angle change to the computer, and adjust the angle of the projected image through the calculation of the computer, so that the image is actually projected on the curing container The angle between the two should be consistent with the angle of the designed image to ensure the accuracy of the printing angle.

Advantages

The advantages of the present invention for newly designed printers are:

1. The use of multiple feeding units and discharging units can easily realize printing with multiple materials, which can better imitate the multi-component characteristics of natural tissues and organs.

2. The feeding port of the feeding unit and the discharging port of the discharging unit are provided outside the bottom of the quartz resin tank, which can minimize the influence of the flow of bio-ink on the formed structure during feeding and discharging.

3. The volume projection imaging principle is used for photo-curing bio-ink, which can realize the integrated printing of the target structure, rather than stacking from top to bottom or from bottom to top. This method can print more complex structures and better mimic the complex structures of natural tissues and organs.

4. During the entire printing process, there is no need to move the quartz resin tank, which can ensure that the shape of the printing structure is more stable.

DETAILED DESCRIPTION OF THE INVENTION

The present invention provides specific implementation examples to illustrate the printing method of the present invention. It can be understood that these examples are only for further explanation of how to implement the present invention, and do not limit the present invention in any way. The scope of the present invention is subject to the claims.

EXAMPLE 1

Fast Batch Printing for 8-Color Colored Micrometer Cubes

Bio-ink preparation: 1) 75 mg ortho-nitrobenzyl modified hyaluronic acid (HA-NB), 250 mg methacrylic anhydride modified gelatin (GelMA) and 10 mg phenyl (2,4,6-trimethyl benzoyl) lithium phosphate (LAP) was dissolved in 10 ml of deionized water to prepare a light-controlled 3D printing ink containing 0.75% HA-NB, 2.5% GelMA and 0.1% LAP.

Figure 1:
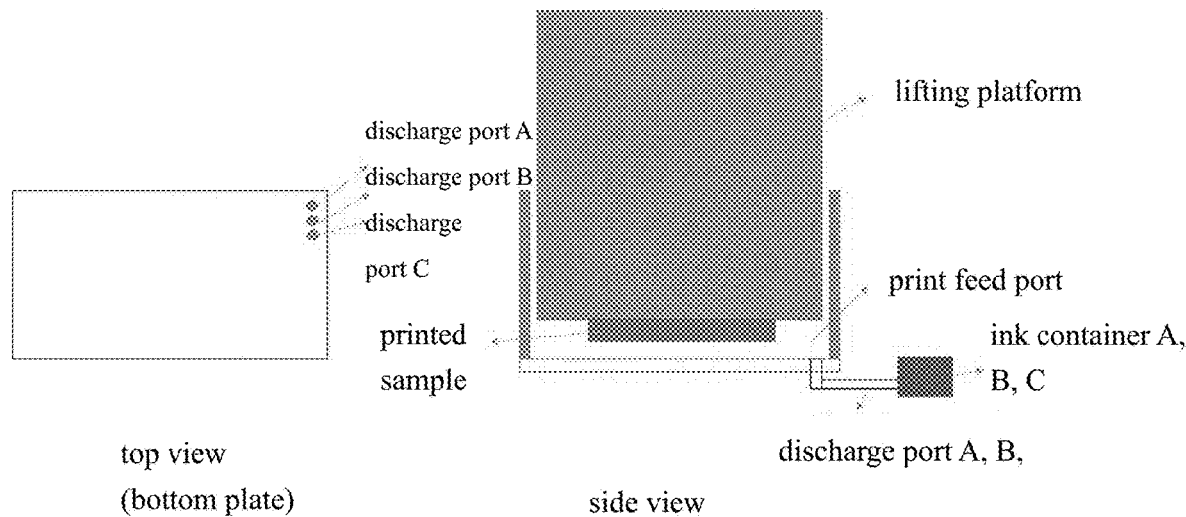
FIG. 1 is a schematic structural view of the feeding system, feed pond and upgrading platform of the present invention.

The structure of the printing device is shown in FIG. 1. The left side is a top view, and the right side is a perspective view. It has three discharge ports A, B, and C to exclude different inks. The lifting platform is located above the printing pool, and the light is projected from below to the printing. In the pool, when printing objects of different materials, it is convenient to exclude different inks, and the type of ink can be easily replaced without causing pollution between the inks. Make printed materials more precise. The type of ink is different, and the structure of the printed object is also complicated.

Figure 2:
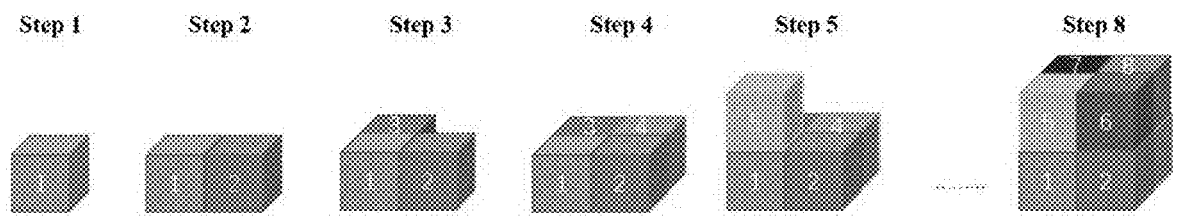
FIG. 2 is a schematic diagram of the process of printing 8-color micrometer cubes.
Figure 3:
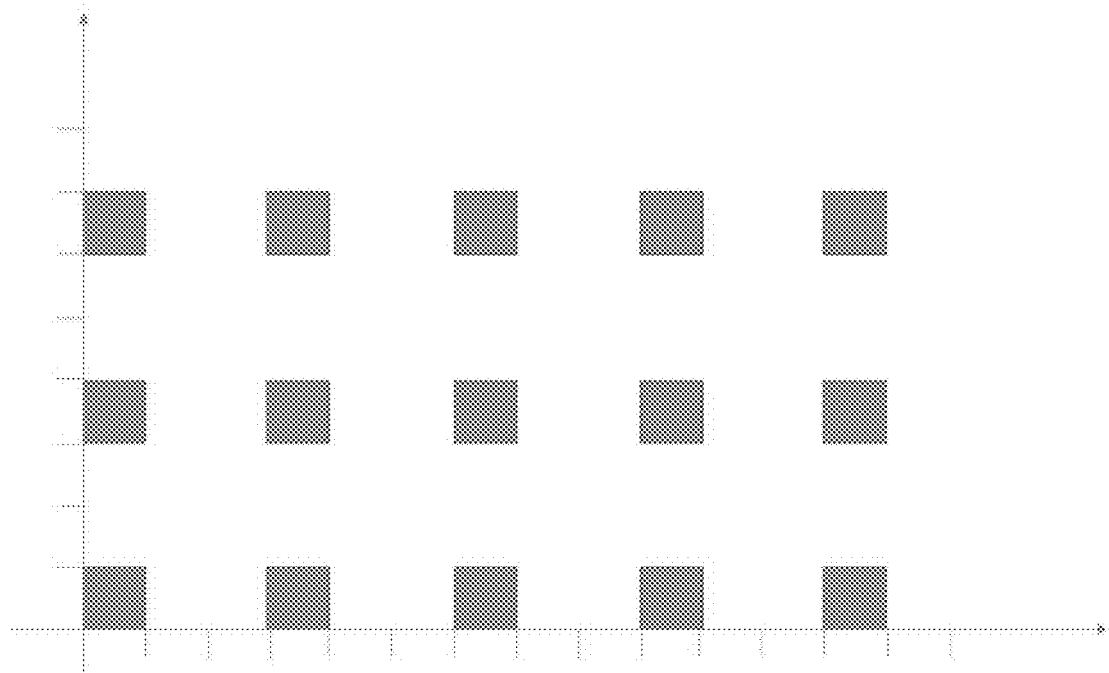
FIG. 3 is a projection picture of the array of unit cubes 1 and 5 in a batch of 8-color micrometer cubes.
Figure 4:
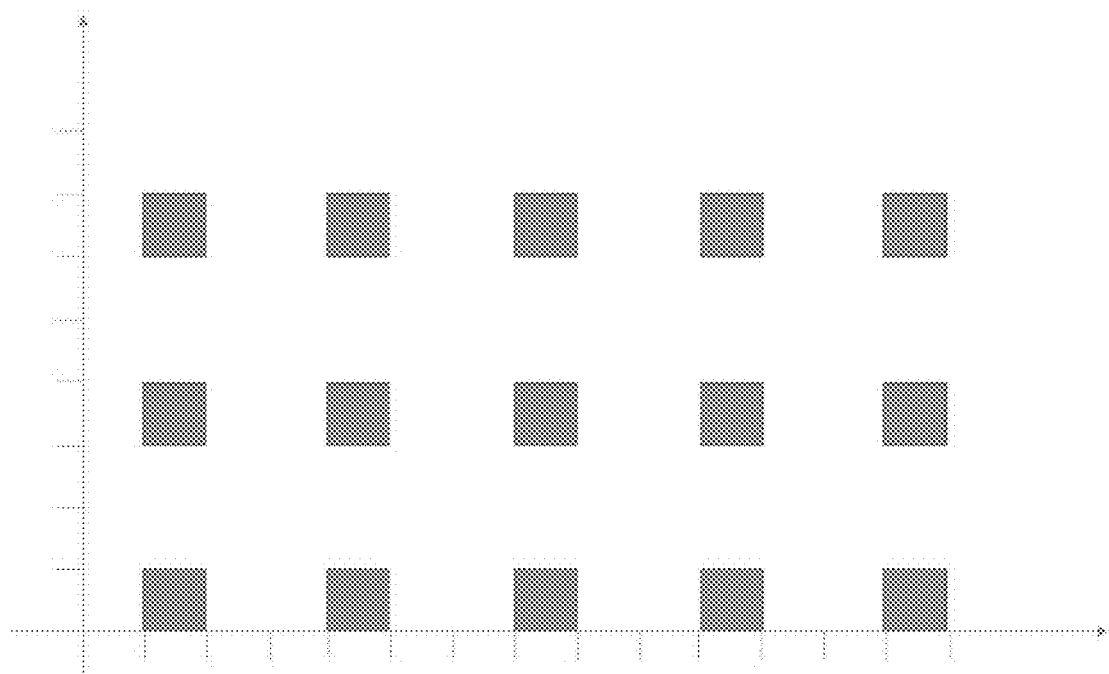
FIG. 4 is a projection picture of the array of unit cubes 2 and 6 in a batch of 8-color micrometer cubes.
Figure 5:
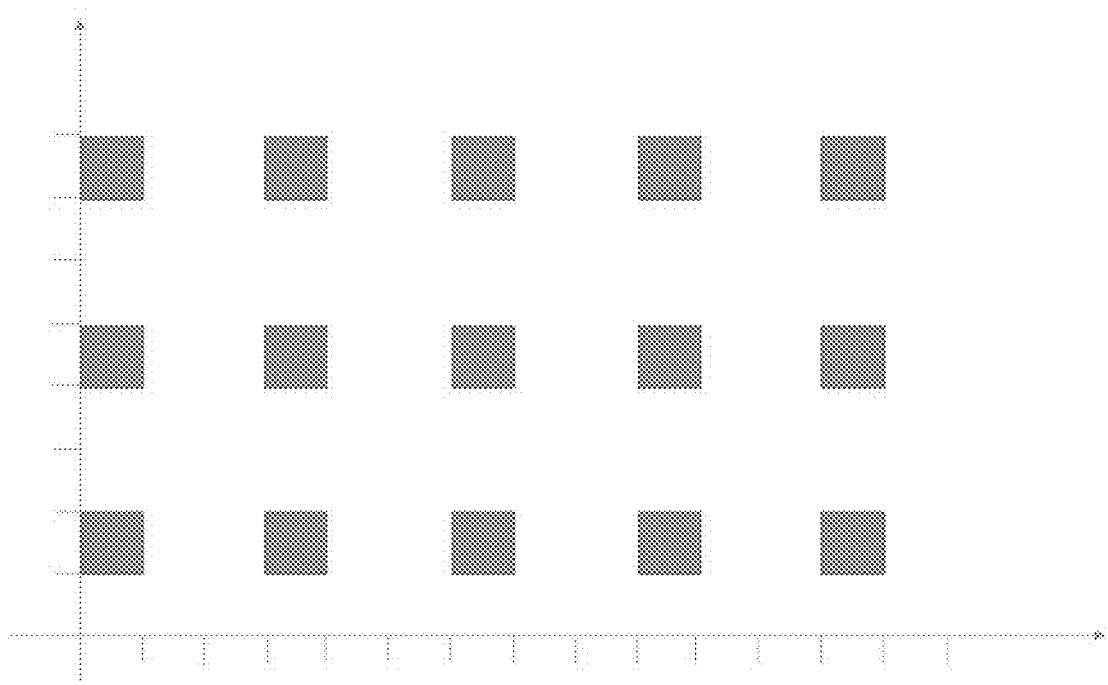
FIG. 5 is a projection picture of batch printing 3 and 7 arrays of unit cubes in 8-color micrometer cubes.
Figure 6:
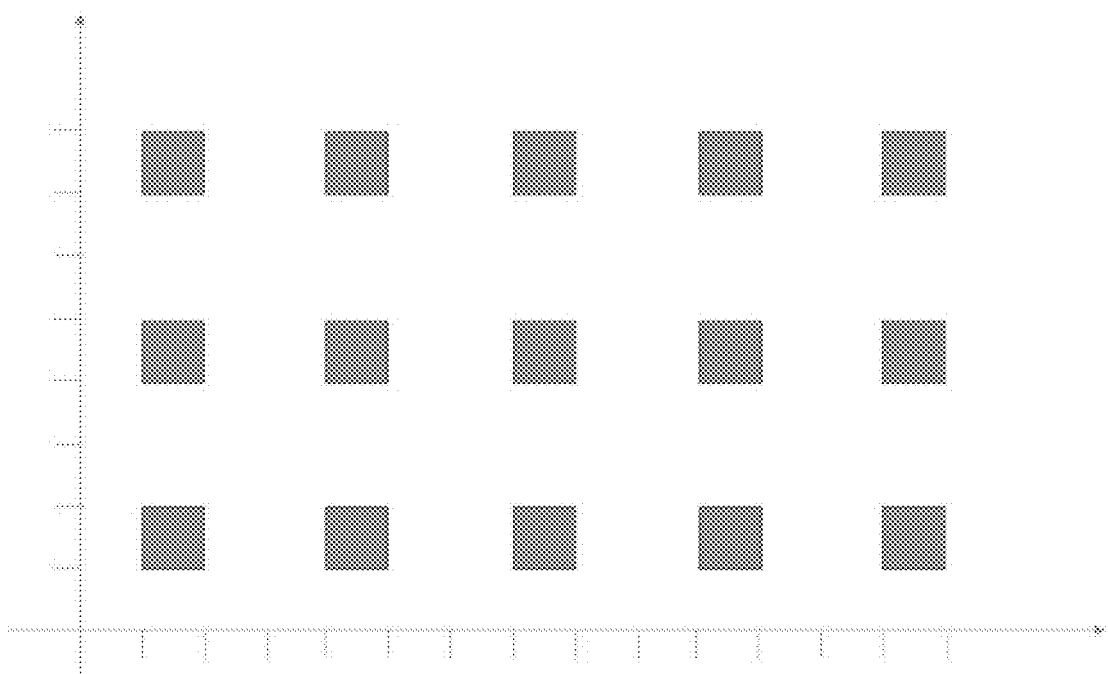
FIG. 6 is a projection picture of batch printing of arrays of unit cubes 4 and 8 in 8-color micrometer cubes.

For example, as shown in FIG. 2, first build a model of four-unit cube arrays, and project images of four-unit cubes as shown in FIGS. 3-6, and then perform program control according to the established model, and then print. The printing steps are as follows:

1. First, set the layer thickness, for example, the unit cube side length is 50 um, then the layer thickness is set to 50 um (number 1 in FIG. 2).

2. Provide a layer of ink A with a thickness of 1 unit and select a cube model for projection exposure printing.

3. Absorb uncured ink A.

4. Keep the layer thickness and height unchanged, for a layer of material B, select the position 2 cube model for projection exposure printing (number 2 in FIG. 2).

5. Absorb uncured ink B.

6. Repeat steps 2~5 until the first layer structure is all printed, and the numbers 3 and 4 in FIG. 2 are printed.

7. The sample platform rises one level.

8. For the two-layer thickness of material E, select the location 1 unit cube model for projection exposure printing (number 5 in FIG. 2).

9. Absorb uncured ink E.

Figure 7:
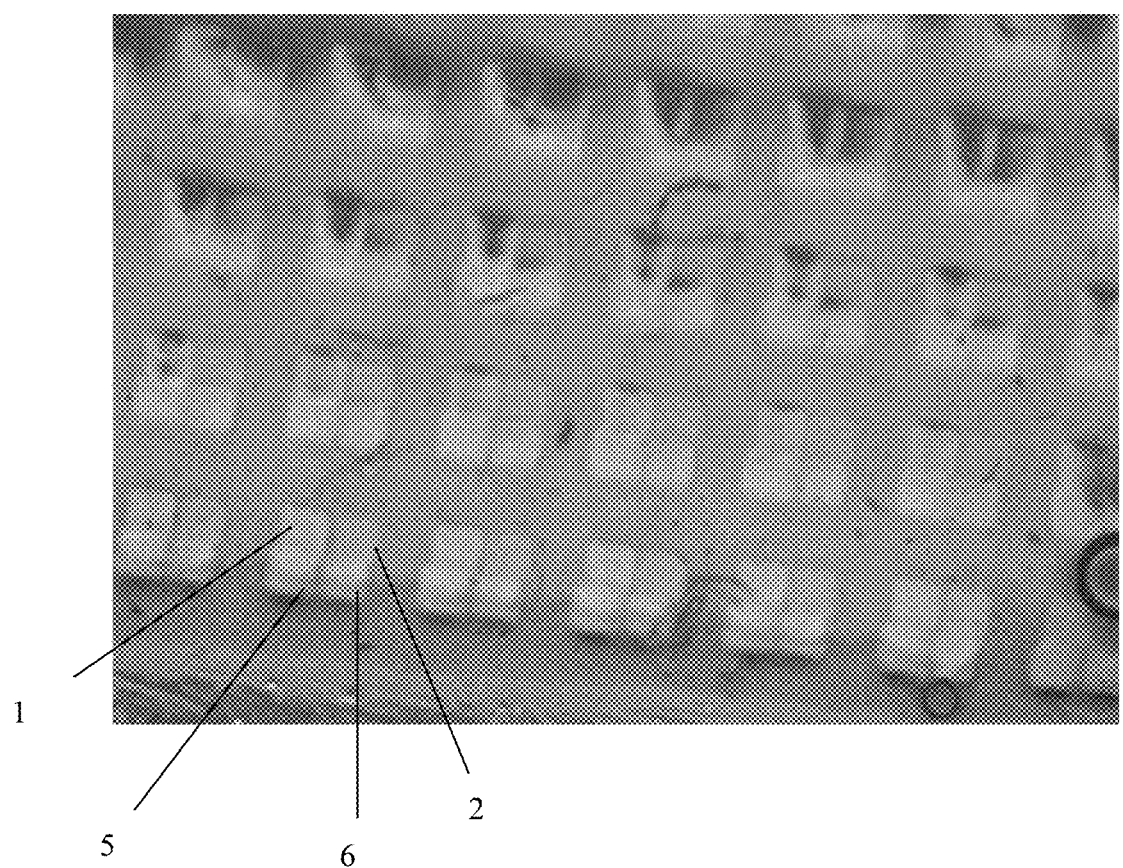
FIG. 7 is an optical microscope photograph of 8-color micrometer cubes printed in batches through the printing process of FIG. 2.

10. Repeat steps 8~9 until the second layer structure is completely printed (numbered 5, 6, 7, 8 in FIG. 2), complete the 8-color color micron cube printing and finally obtain the 8-color color batch printing as shown in FIG. 7, the exposure light intensity is 50, and the exposure time of each layer is 1000 ms. This can facilitate the structure of color printing. Among them, the symbols 1, 5, 6, 2 indicate the structure formed by different inks.

The image projection here can adopt the image processing unit of this invention to perform image processing in the early stage, and then output through the projection device, project into the printing pool, and directly perform light curing on the projected image. For example, the different numbers in FIG. 2 may all be one projection image, and the projection image is just a plurality of identical images superimposed and printed. For example, the number 1 has 50 um, the thickness of each image printed is 5um, then 10 identical images are continuously projected for light curing, and then the number 1 can be printed. By analogy, when the number 2 is another bio-ink, 10 identical projection images 2 are printed with different bio-inks, and the printing of the number 2 is obtained. In this way, if the inks of number 1 and number 2 are different, the materials are different. According to this understanding, this method is more complicated, but the printed structure is more complicated, closer to the structure of the organism itself, and possibly provides for the replacement of human organs.

EXAMPLE 2

3D Printed Cartilage Scaffold for Repairing Osteochondral Defects

Figure 8:
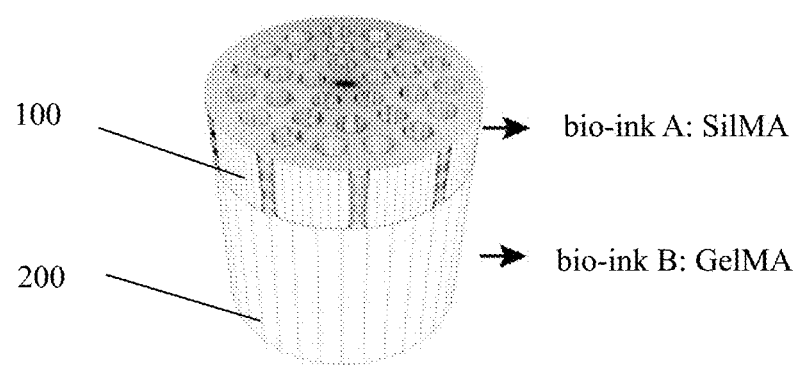
FIG. 8 is a schematic diagram of a three-dimensional modeling three-dimensional structure of a printing body according to an embodiment of the present invention.
Figure 9:
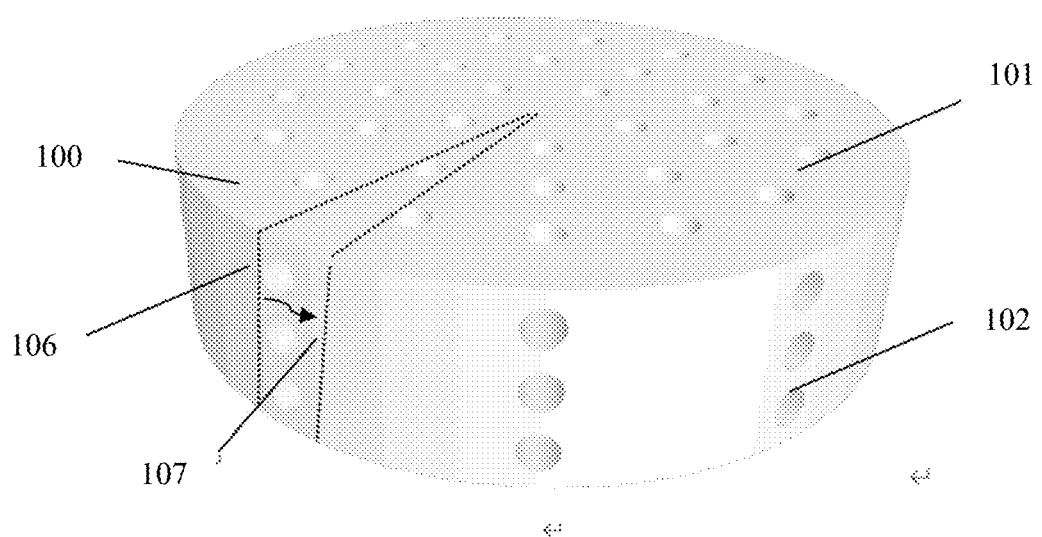
FIG. 9 is a three-dimensional model diagram of the superstructure of the structure shown in FIG. 8.
Figure 10:
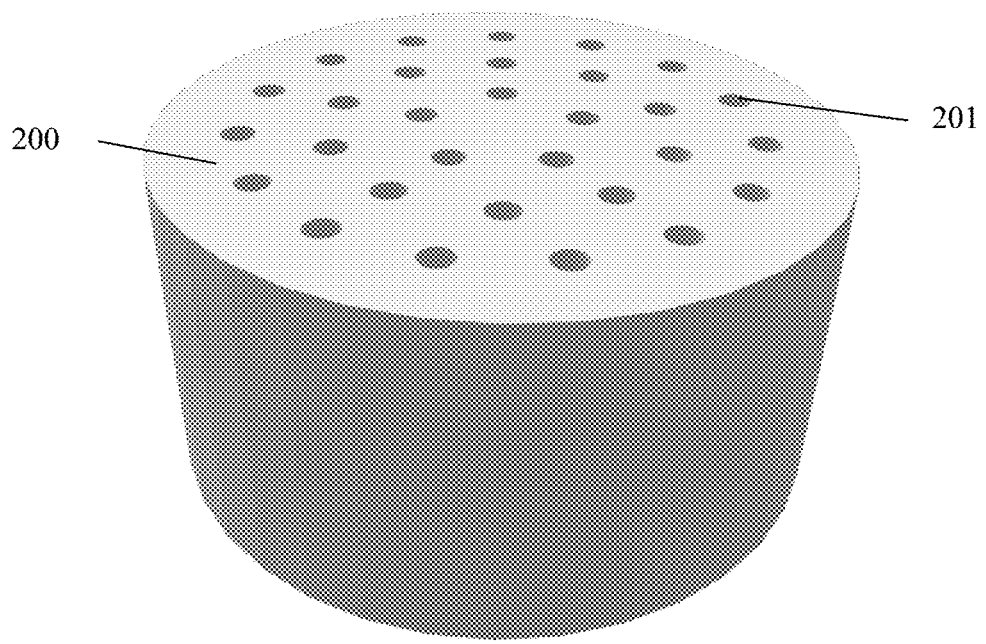
FIG. 10 is a three-dimensional model diagram of the lower structure of the structure shown in FIG. 8.

For example, as shown in FIGS. 8, 9, and 10, the target structure to be printed is first modeled, and then program control is performed according to the established model to perform "colorful" volume imaging printing of different materials of different parts of the scaffold.

For example, the created models are shown in FIGS. 8, 9 and 10. FIG. 8 is a cartilage scaffold model, which consists of two parts, the upper scaffold of FIG. 9 and the lower scaffold of FIG. 10, respectively. The upper scaffold has 30 circular holes in plan view, and 30 circular holes on the side, and each circular hole intersects with each other.

Figure 11:
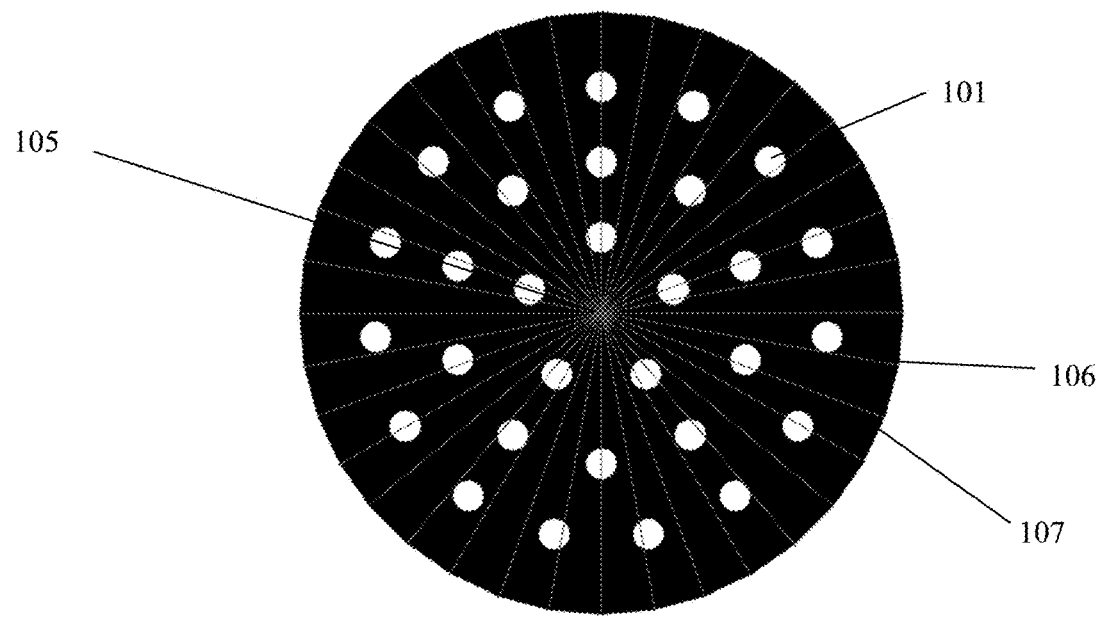
FIG. 11 is a schematic diagram of a division method of image processing of the upper layer structure of FIG. 8.
Figure 12:
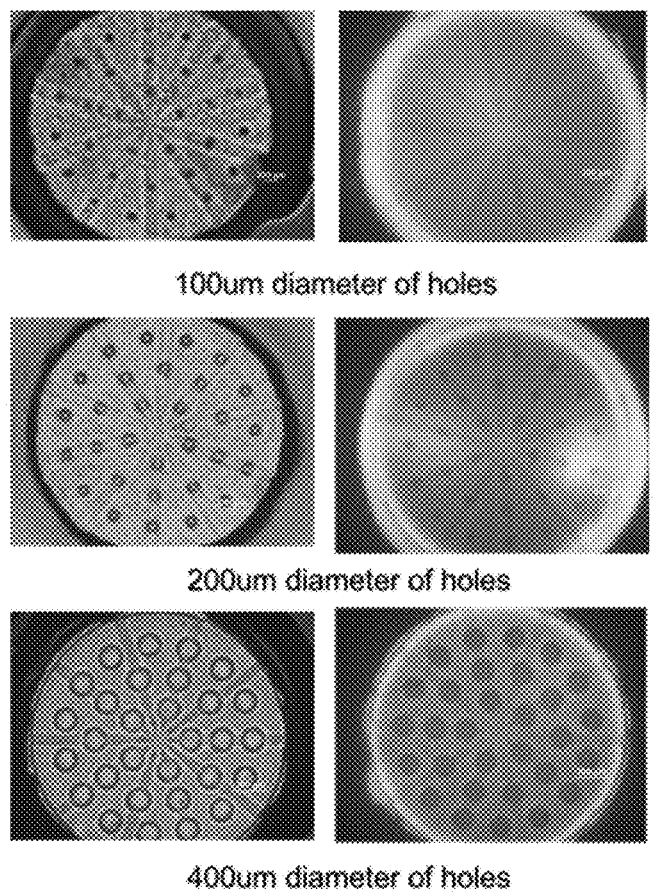
FIG. 12 is a photomicrograph of a physical image of the structure shown in FIG. 8 printed by the printing method of the present invention.
Figure 13:
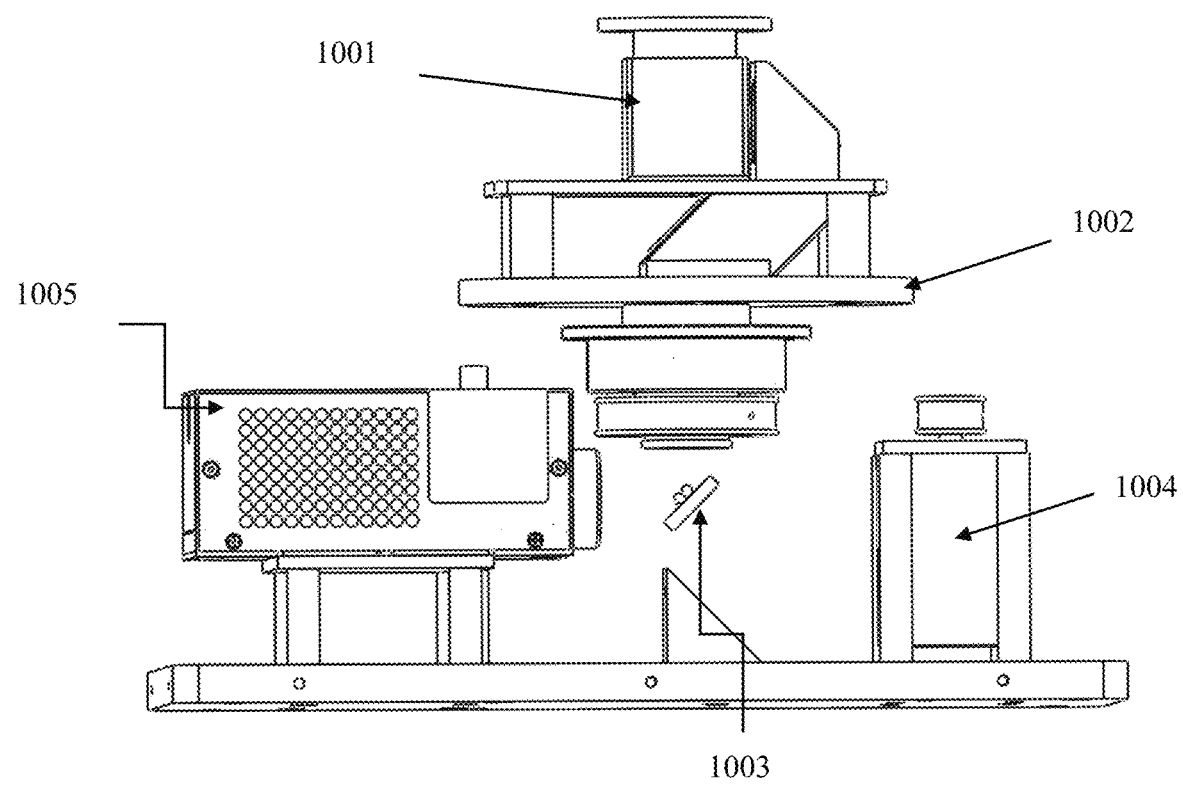
FIG. 13 is a perspective structural view of a printing apparatus in a specific embodiment of the present invention.
Figure 14:
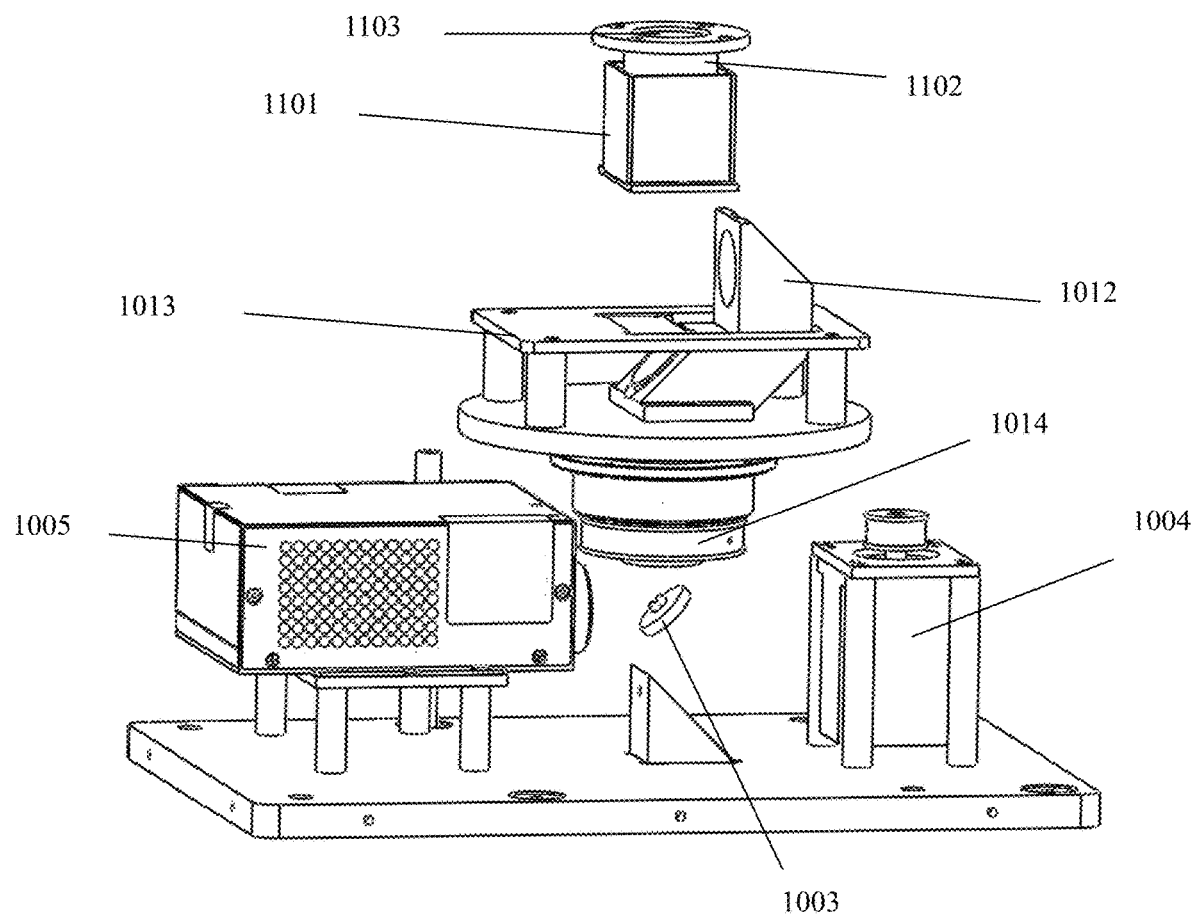
FIG. 14 is an exploded structural diagram of a printing apparatus in a specific embodiment of the present invention.
Figure 15:
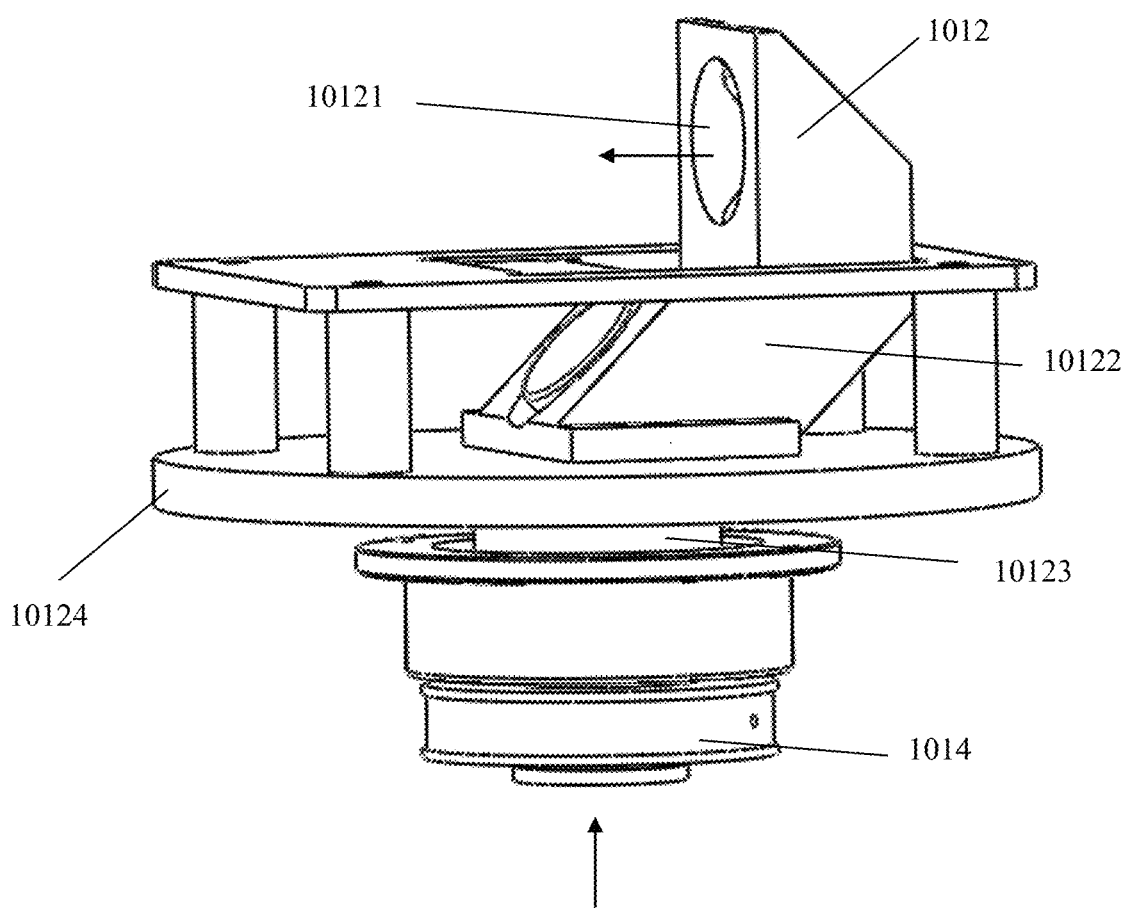
FIG. 15 is a schematic diagram of a stereo structure of an optical path conversion unit that can move relatively in a specific embodiment of the present invention.
Figure 16:
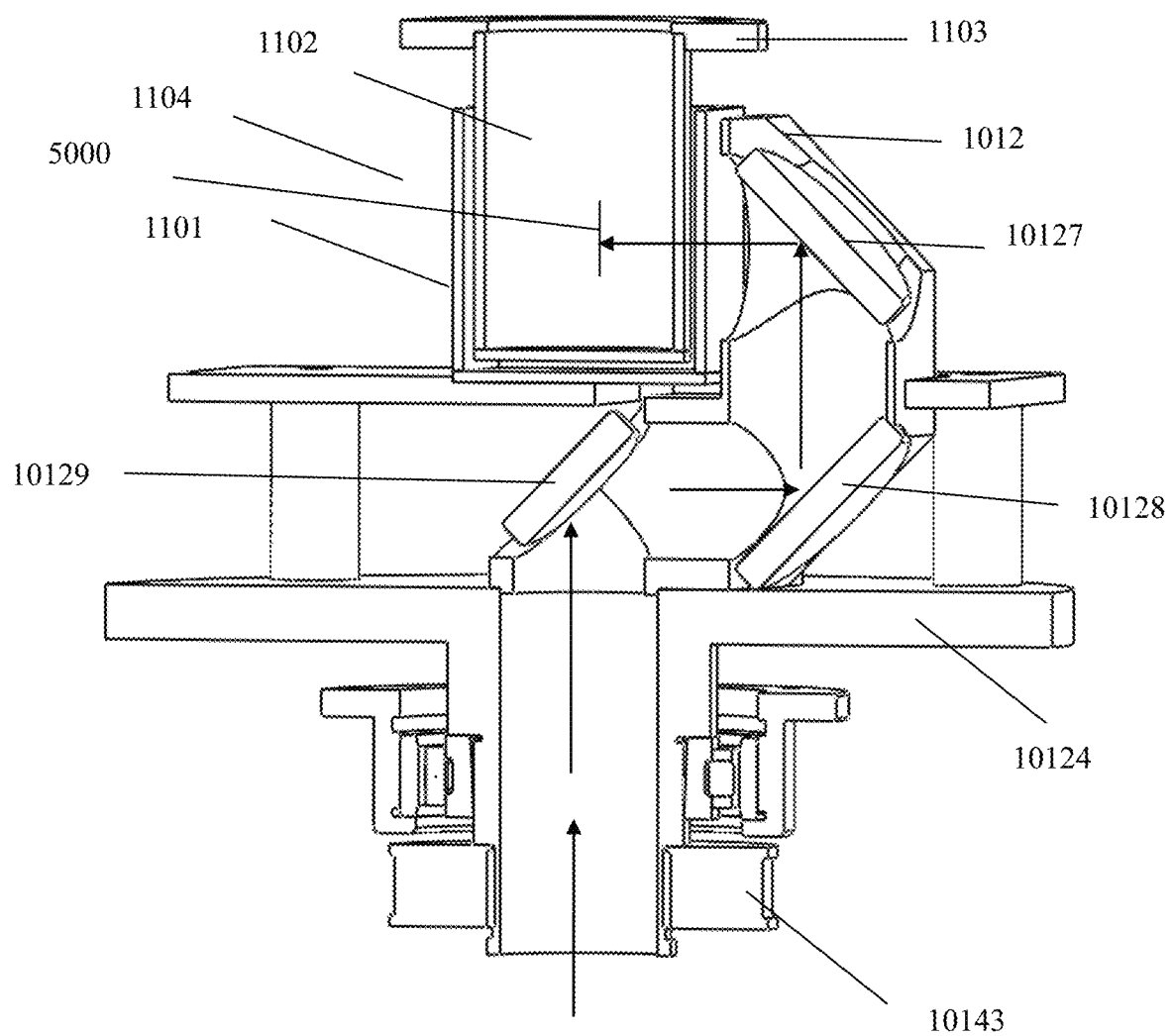
FIG. 16 is a cross-sectional view of a relatively moving optical path conversion unit and a cross-sectional structure diagram of a curing container in a specific embodiment of the present invention.
Figure 17:
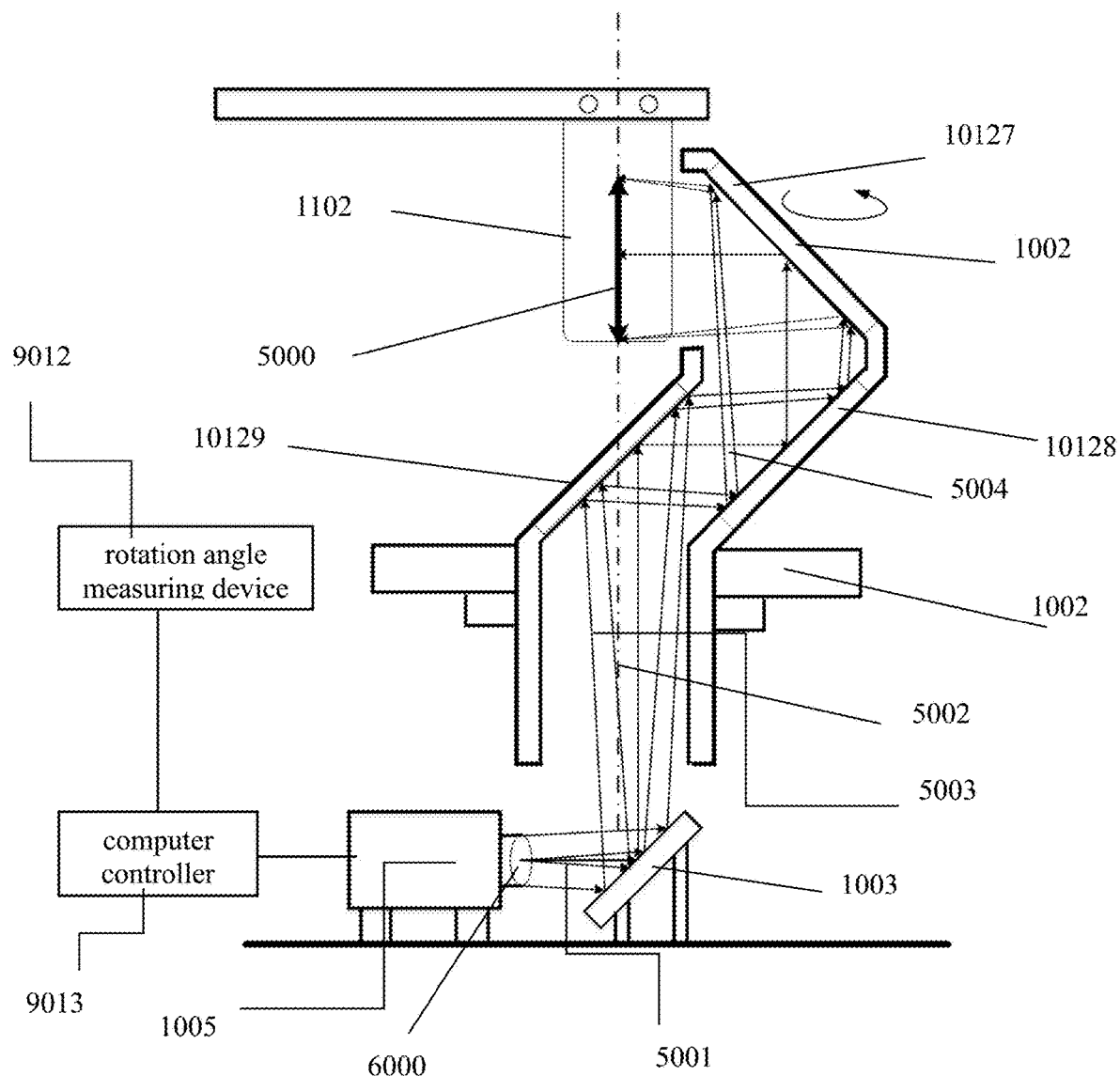
FIG. 17 is a schematic diagram of the principle of optical path change in a specific embodiment of the present invention.
Figure 18:
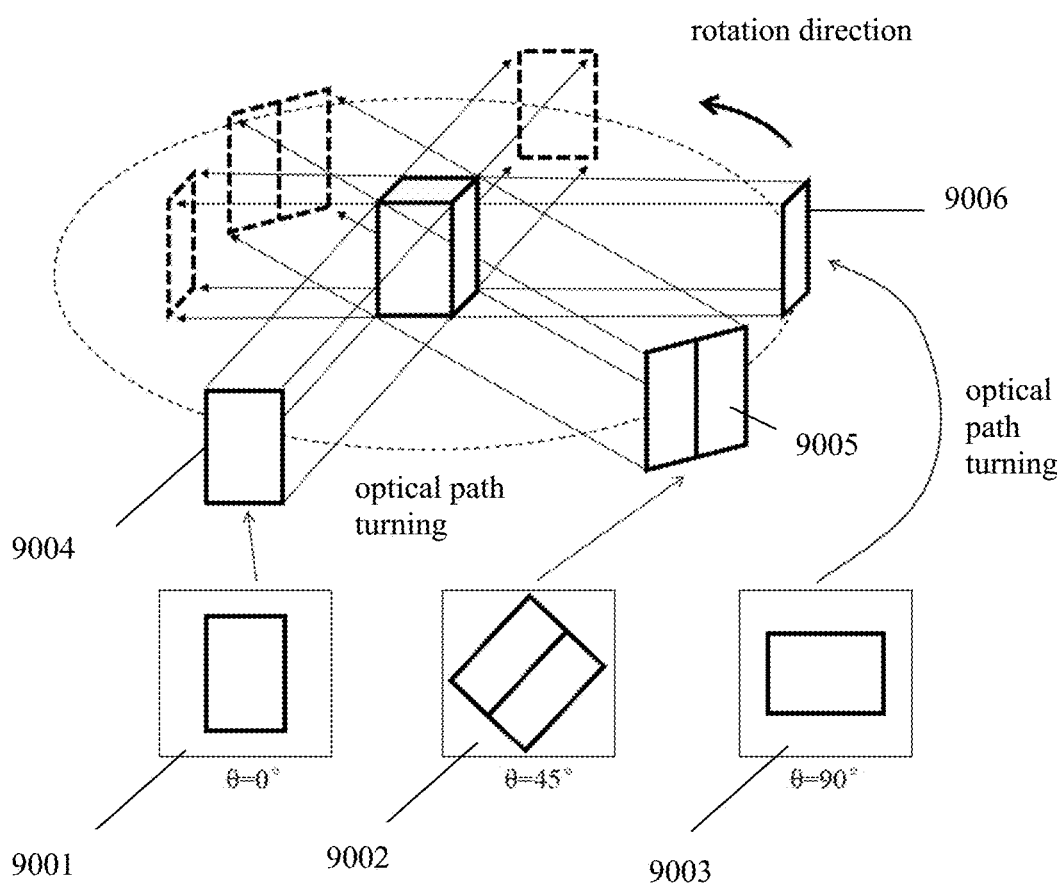
FIG. 18 is a schematic diagram of the principle of adjusting the angle of a projected image.
Figure 19:
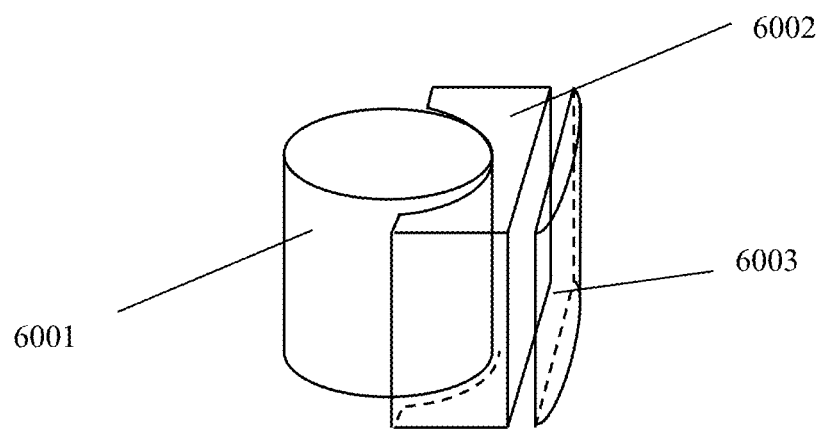
FIG. 19 is a schematic structural view of keeping the direction of light of the projected image unchanged.
Figure 20:
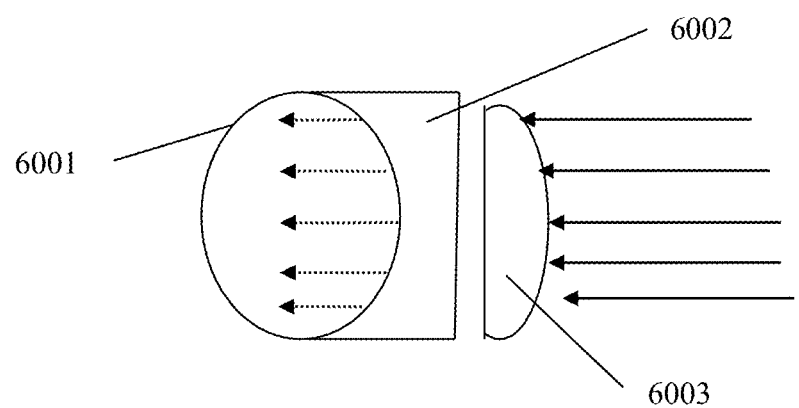
FIG. 20 is a top view of the structure of FIG. 19.
Figure 21:
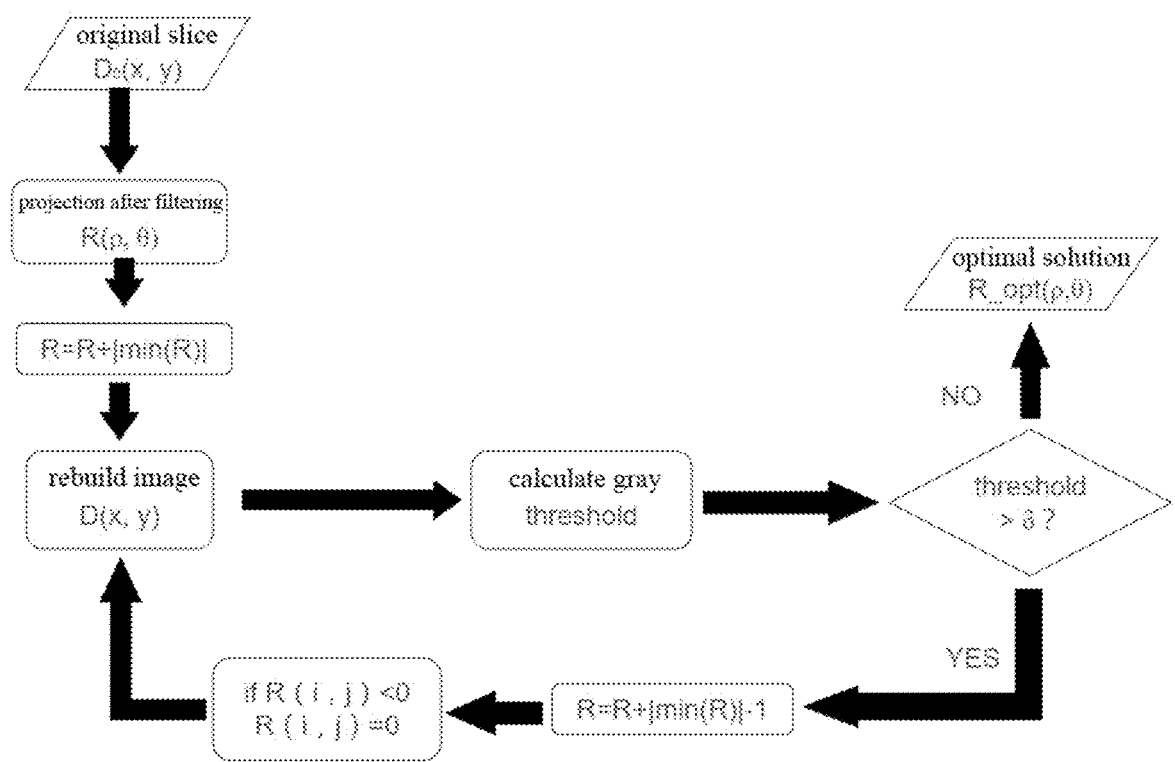
FIG. 21 is a schematic diagram of a method for performing image processing on an angle change measured by a rotation angle.

Taking the above layer structure as an example, the cutting method of the model in this scheme is shown in FIG. 11. The image is cut along the center point 105, and digital information is input in the image processing system. The cutting position can be longitudinal cutting 106, cutting at different angles along the entire cylinder 100. For example, cutting at an angle of 1 degree per arc, in fact, it is cut into countless rectangular parallelepiped faces, but only some faces have no gaps, and some surfaces have gaps. The positions without gaps indicate that no holes are formed, and the gapped positions have holes. The notch can be inside the cuboid or on the edge of the long side. For example, cutting every 1° can actually form 360 faces. When cutting at an angle of 0.5°, 720 faces are formed. Cutting image can be automatically completed in the software, so that the digital information of different faces is formed, and very accurate image construction can be achieved. The digital information is delivered by the projector. Each projection is a cut surface. The light on the surface is reflected by the light and irradiated into the container with bio-ink. An image of the cut surface is formed in the container of bio-ink. Curing is required for curing with focused light, while unfocused light can pass through the bio-ink without curing. In this way, a rectangular parallelepiped surface is formed in the bio-ink, because the 360-degree dimension is performed, so after each cured surface is formed, the optical path system needs to be rotated to change the focus position, and the 360° is completed as the rotation continues. The focusing and curing of multiple different surfaces are completed, and finally completes the printing of the entire model.

If different tissues or structures, or the structure of each face is different, the first bio-ink can be excluded after forming one face and new different bio-ink can form another face. This face can be of different heights, different thicknesses, or a face with a different structure. In this way, color printing can be easily achieved.

This design is to use the scaffold for cartilage repair. The top view of the lower scaffold has 30 holes. The purpose of this design is to allow the bone marrow mesenchymal stem cells to migrate to the upper layer and help repair the cartilage. For the design of the upper scaffold, the middle hole is for the bone marrow mesenchymal stem cells to migrate to the cartilage layer, and the side holes are for the chondrocytes to migrate to the injured area, to better repair the cartilage defects.

The ratios of the bio-inks used in the upper and lower layers of the scaffold structure are as follows:

Upper layer ink: The upper layer is methacrylic anhydride grafted silk fibroin (SilMA) with a concentration of 15%. The concentration of photosensitizer is 10% v/v, and the concentration of phenol red is 0.8%;

Lower layer ink: the lower layer is 8M methacrylic anhydride grafted gelatin (GelMA) with a concentration of 15%. The concentration of photosensitizer is 10% v/v and the phenol red concentration is 0.8%. Configuration process:

The printing process is described using two biomaterials according to the model shown in FIG. 8 as follows: the lower layer scaffold is integrally formed first, and the upper layer scaffold is then integrally formed as an example. The printing process using two biological materials according to the cartilage scaffold model is as follows:

Image Processing:

Modeling with C4D software to create a target printing structure, for example, it can be a columnar structure with two layers on top and bottom, as shown in FIG. 8 on both sides of the structure, or three-dimensional construction of different structures, or any of the internal structure can be achieved.

2. Separate the upper and lower layers of the model, and export them to the upper structure (upper.stl) and lower structure (bottom.stl) format files, as shown in FIG. 9 and FIG. 10.

3. Use software Matlab to read the upper and bottom .stl files.

4. Use the Image Processing Toolbox in the software Matlab to segment the images of the upper and bottom 3D models.

5. Use the Image BlendingPackage in software Matlab to fuse the two models of upper and bottom, and make the holes correspond.

6. Find the central symmetry axis of the upper and bottom models, make a plane containing the symmetry axis, and output the mapping of the 3D model on the plane;

7. Rotate the plane in a clockwise direction and cut every certain angle. As shown in FIG. 11, after the cutting process is cycled, the result file after the processing is completed.

Step 1: Slice the upper and lower layers of the 3D cartilage scaffold model separately, and the graphics of each slice are used as the lighting graphics of the layer; the two bio-inks are respectively loaded into the feeding unit according to the needs of the printed object, and the lower slice is initially projected the bottom of the obtained image is flush with the bottom surface of the resin tank.

Step 2: The feeding unit 1 with GelMA injects bio-ink GelMA into the resin tank from below the quartz resin tank. The height of the bio-ink is slightly larger than the height of the underlying structure. In fact, the height of the ink is consistent with the height of the formed structure and the volume is consistent or the shape is similar). The stepping motor 1004 drives the reflecting mirrors 10129, 10128, 10127 and the square box 1101 to rotate synchronously, and the projector 1005 and the ink container 110, 2 and resin tank are fixed. The reflecting mirror and the rotation centers of square box coincide with resin tank's geometric center 5002. According to the preset angle interval of the image processing system, each time the stepping motor rotates through an angle, it drives the mirror and the square box to rotate by an angle in the same direction. At the same time, the projector quickly switches to the next projected image to complete a projection direction Exposure. After 360° exposure, a specific exposure amount distribution will be formed in the resin tank, and the position with exceeding bio-ink GelMA light curing exposure threshold will be cured and formed, and the remaining positions will still be liquid, and the printing of the underlying structure will be completed. The lens 1003 here is also fixed.

Step 3: The discharge unit draws away all uncured bio-ink GelMA from the bottom of the resin tank. Then, the supply unit 2 equipped with SilMA injects the bio-ink SilMA into the curing container 11021 from below the quartz resin tank, such as a resin tank. The height of the bio-ink is slightly larger than that corresponding to the resin tank on the top surface of the superstructure. At this time, there is a small amount of overlap between the projection of the upper structure and the upper portion of the lower structure to ensure a stable connection between the upper and lower structures. The stepping motor drives the reflecting mirror and square box to rotate synchronously, and the projector and curing container do not move. The rotation centers of the reflecting mirror and the square box coincide with the geometric center 5002 of the resin tank. According to the preset angle interval of the image processing system, each time the stepping motor rotates through an angle, it drives the reflecting mirror and the square box to rotate by an angle in the same direction. At the same time, the projector quickly switches to the next projected image to complete a projection direction Exposure. After 360° exposure, a specific exposure amount distribution will be formed in the resin tank, and the position exceeding the bio-ink SilMA light curing exposure threshold will be cured and formed, and the remaining positions will still be liquid for printing of the superstructure.

Step 4: The discharge unit draws all uncured bio-ink SilMA from the bottom of the resin tank. The entire scaffold is printed.

FIG. 11 is a microstructure diagram of each layer. Among them, it can be seen from the top views of different cavity sizes that the side holes and the top holes are arranged in the same way. At the same time, the fluorescence structure of 400 um was observed under a fluorescence microscope.

In the absence of any elements and limitations specifically disclosed herein, the invention shown and described herein can be implemented. The terms and expressions are used as illustrative terms and not as limitations, and it is not intended that the use of these terms and expressions exclude any equivalents of the features and parts shown and described or parts thereof, and it should be recognized that each such modifications are possible within the scope of the present invention. Therefore, it should be understood that although the present invention is specifically disclosed through various embodiments and optional features, modifications and variations of the concepts described herein can be adopted by those of ordinary skill workers in the field, and these modifications and variations are considered to fall into the scope of the invention as defined in the appended claims is within the scope of the invention.

The invention claimed is:

1. An imaging principle-based integrated color light 3D bioprinting system, comprising:
    an optical imaging unit configured to allow a printed subject to form one or more optical images;
    an optical path conversion unit configured to allow an imaging optical path of the one or more optical images to be projected into a bio-ink capable of being cured by light, so that the light allows the projected imaging optical path to cure the bio-ink by focus of the light;
    a curing container, wherein the bio-ink is in a liquid form and carried in the curing container, the curing container is fixed, the optical path conversion unit is arranged to rotate relative to the curing container, the optical path conversion unit comprises a lens and a reflecting mirror, the lens converts the light from a projection unit into parallel light, and the reflecting mirror is configured to project the parallel light vertically into the curing container, wherein a movement of the optical path conversion unit includes a continuous peripheral movement of the optical path conversion unit around the curing container; and
    a rotation angle detection device connected to the reflecting mirror, wherein the rotation angle detection device continuously monitors a horizontal rotation angle of the reflecting mirror in real time during rotation and enters an actual angle into a computer control system, such that the computer control system calculates and allows a projection angle to be compensated in advance to ensure that a light angle of the projected optical images does not change after passing the lens and the reflecting mirror.

2. The bioprinting system according to claim 1, wherein the optical imaging unit comprises an image processing unit and the projection unit, wherein the image processing unit converts the printed subject into a digital signal, and the one or more optical images are generated by the projection unit.

3. The bioprinting system according to claim 2, wherein the printing subject is generated in a form of a three-dimensional modeling, and the image processing unit cuts graphics of the three-dimensional modeling in different dimensions.

4. The bioprinting system according to claim 3, wherein cutting in different dimensions includes cutting and decomposition along a central peripheral axis of the one or more optical images.

5. The bioprinting system according to claim 4, wherein the cutting further comprises cutting with different curvatures along a circumference of the one or more optical images.

6. The bioprinting system according to claim 5, wherein the projection unit projects the one or more optical images formed by cut surfaces.

7. The bioprinting system according to claim 1, wherein the peripheral movement is a 360-degree movement.

8. The bioprinting system according to claim 1, wherein a glass prism and/or a cylindrical lens are provided outside the curing container.

9. The bioprinting system according to claim 8, wherein the glass prism and/or the cylindrical lens and the optical path conversion unit move synchronously.

10. The bioprinting system according to claim 1, wherein the optical path conversion unit is configured to make a circular movement around the curing container.

11. The bioprinting system according to claim 1, wherein the bio-ink comprises a light-responsive cross-linking group modified macromolecule, ortho-nitrobenzyl phototrigger modified macromolecule, and a light initiator.

\* \* \* \* \*